United States Patent
Wu et al.

(10) Patent No.: US 11,737,688 B2
(45) Date of Patent: Aug. 29, 2023

(54) APPARATUS AND METHODS OF PROBING SENSOR OPERATION AND/OR DETERMINING ANALYTE VALUES DURING CONTINUOUS ANALYTE SENSING

(71) Applicant: Ascensia Diabetes Care Holdings AG, Basel (CH)

(72) Inventors: Huan-Ping Wu, Granger, IN (US); Mark D. Cerutti, Yonkers, NY (US)

(73) Assignee: Ascensia Diabetes Care Holdings AG, Basel (CH)

(*) Notice: Subject to any disclaimer, the term of this patent is extended or adjusted under 35 U.S.C. 154(b) by 562 days.

(21) Appl. No.: 16/782,974

(22) Filed: Feb. 5, 2020

(65) Prior Publication Data
US 2020/0245911 A1    Aug. 6, 2020

Related U.S. Application Data

(60) Provisional application No. 62/801,592, filed on Feb. 5, 2019.

(51) Int. Cl.
*A61B 5/1455*    (2006.01)
*A61B 5/145*    (2006.01)
(Continued)

(52) U.S. Cl.
CPC .......... *A61B 5/14532* (2013.01); *A61B 5/002* (2013.01); *A61B 5/01* (2013.01);
(Continued)

(58) Field of Classification Search
CPC .......................... A61B 5/14532; A61B 5/1455
See application file for complete search history.

(56) References Cited

U.S. PATENT DOCUMENTS 5,792,668 A    8/1998    Fuller et al.
8,233,958 B2    7/2012    Brauker et al.
(Continued)

FOREIGN PATENT DOCUMENTS

CA    3061574 A1    1/2019
CA    3061574 C    7/2022
(Continued)

OTHER PUBLICATIONS

Stein et al.: "Microscale Enzymatic Optical Biosensors Using Mass-Transport Limiting Nanofilms. 1. Fabrication and Characterization Using Glucose as a Model Analyte"; Anal Chem. Feb. 15, 2007; 79(4): 1339-1348. DOI: 10.1021/ac061414z; https://www.ncbi.nlm.nih.gov/pmc/articles/PMC2518633/.
(Continued)

*Primary Examiner* — Marjan Fardanesh
(74) *Attorney, Agent, or Firm* — Erise IP, P.A.

(57) ABSTRACT

Apparatus and methods are operative to probe the condition of a sensor either initially, at any point thereafter or continuously during a continuous sensor operation for measuring an analyte in a bodily fluid (such as performed by, e.g., a continuous glucose monitoring (CGM) sensor). Results of the probe may include calibration indices determined from electrical signals obtained during the probe. The calibration indices may indicate whether in-situ adjustment of the sensor's calibration should be performed either initially and/or at random check points. Probing potential modulation parameters also may be used during analyte calculations to reduce the effects of lot-to-lot sensitivity variations, sensitivity drift during monitoring, temperature, interferents, and/or the like. Other aspects are disclosed.

37 Claims, 23 Drawing Sheets

(51) Int. Cl.
    *A61B 5/01*     (2006.01)
    *A61B 5/00*     (2006.01)
    *A61B 5/1486*     (2006.01)
    *A61B 5/1495*     (2006.01)
    *A61M 5/172*     (2006.01)

(52) U.S. Cl.
    CPC .......... *A61B 5/1486* (2013.01); *A61B 5/1495* (2013.01); *A61B 2560/0223* (2013.01); *A61B 2560/0238* (2013.01); *A61M 2005/1726* (2013.01)

(56) References Cited

U.S. PATENT DOCUMENTS

| | | |
|---|---|---|
| 8,583,205 B2 | 11/2013 | Budiman et al. |
| 2006/0094946 A1 | 5/2006 | Kellogg et al. |
| 2007/0167867 A1 | 7/2007 | Wolf |
| 2007/0270675 A1 | 11/2007 | Kane et al. |
| 2008/0077015 A1 | 3/2008 | Boric-Lubecke et al. |
| 2008/0234562 A1 | 9/2008 | Jina |
| 2012/0197576 A1 | 8/2012 | Feldman |
| 2012/0265035 A1 | 10/2012 | Bohm et al. |
| 2012/0283538 A1 | 11/2012 | Rose et al. |
| 2013/0071869 A1 | 3/2013 | Wu |
| 2013/0256156 A1 | 10/2013 | Wu et al. |
| 2014/0209460 A1 | 7/2014 | Wu et al. |
| 2014/0273042 A1 | 9/2014 | Saint |
| 2015/0073718 A1 | 3/2015 | Elder et al. |
| 2015/0198555 A1 | 7/2015 | Lee et al. |
| 2015/0351673 A1 | 12/2015 | Vanslyke et al. |
| 2018/0275089 A1 | 9/2018 | Huang et al. |
| 2019/0008426 A1 | 1/2019 | Shiwaku |
| 2019/0125225 A1 | 5/2019 | Rebec et al. |
| 2020/0268290 A1 | 8/2020 | Zach et al. |
| 2020/0268323 A1 | 8/2020 | Zach et al. |

FOREIGN PATENT DOCUMENTS

| | | |
|---|---|---|
| CN | 108778125 A | 11/2018 |
| EP | 1218532 A1 | 7/2002 |
| EP | 1218532 B1 | 7/2002 |
| EP | 1702561 A2 | 9/2006 |
| WO | WO2001088534 A | 11/2001 |
| WO | WO2008079435 A2 | 7/2008 |
| WO | WO2014128638 A1 | 8/2014 |
| WO | WO2017156584 A1 | 9/2017 |

OTHER PUBLICATIONS

Haxha et al.: "Optical Based Noninvasive Glucose Monitoring Sensor Prototype"; University of Bedfordshire, Luton, U.K.; IEEE Photonics Journal: vol. 8, No. 6, Dec. 2016. DOI: 10.1109/JPHOT. 2016.2616491 1943-0655.

Parkes et al.: "A New Consensus Error Grid to Evaluate the Clinical Significance of Inaccuracies in the Measurement of Blood Glucose"; Diabetes Care, vol. 23, No. 8, Aug. 2000.

Provisional Search Report and Written Opinion of related International Application No. PCT/EP2020/052673 dated Apr. 17, 2020.

Nakata, S. et al.: Discrimination of Glucose from Its Interferences Using an Amperometric Sensor Based on Electrochemical Nonlinearity, Analytical Chemistry, 1998 70 (20), 4304-4308 (Year: 1998).

International Search Report and Written Opinion of related International Application No. PCT/EP2020/052673 dated Jul. 9, 2020.

Nakata et al., "Discrimination of Glucose from Its Interferences Using an Amperometric Sensor Based on Electrochemical Nonlinearity", Analytical Chemistry, American Chemical Society, US, vol. 70, No. 20, Oct. 15, 1998, pp. 4304-4308, XP000789048, ISSN: 0003-2700, DOI: 10.1021/AC980442H.

Bond et al., "An integrated instrumental and theoretical approach to quantitative electrode kinetic studies based on large amplitude Fourier transformed a.c. volatammetry: A mini review", Electrochemistry Communications, Elsevier, Amsterdam, NL, vol. 57, May 8, 2015, pp. 78-83, XP029212452, ISSN: 1388-2481, DOI: 10.1016/J.Elecom.2015.04.017.

Nakata et al., "Experimental Demonstration and Simulation of Electrochemical Non-linear Reponses to Glucose and Its Interferents with an Amperometric Senso", Analyst, London, GB, vol. 124, No. 8, Aug. 1, 1999, pp. 1175-1179, XP001039882, DOI: 10.1039/A903187A.

International Preliminary Report on Patentability of International Application No. PCT/EP2020/052673 dated Aug. 19, 2021.

Xu, Liang, et al.: "Optimization method for simultaneous kinetic analysis", Analystical Chem. 1996 ACS, Washington, DC, USA, vol. 68, No. 11, Jun. 1, 1996.

U.S. Appl. No. 17/014,947, filed Sep. 8, 2020, Wu.

U.S. Appl. No. 17/014,962, filed Sep. 8, 2020, Wu.

Chinese Patent Application 202080016885.8 Office Action and Search Report dated May 7, 2023.

Taiwan Patent Application 109103528 Official Letter and Search Report dated Jun. 5, 2023.

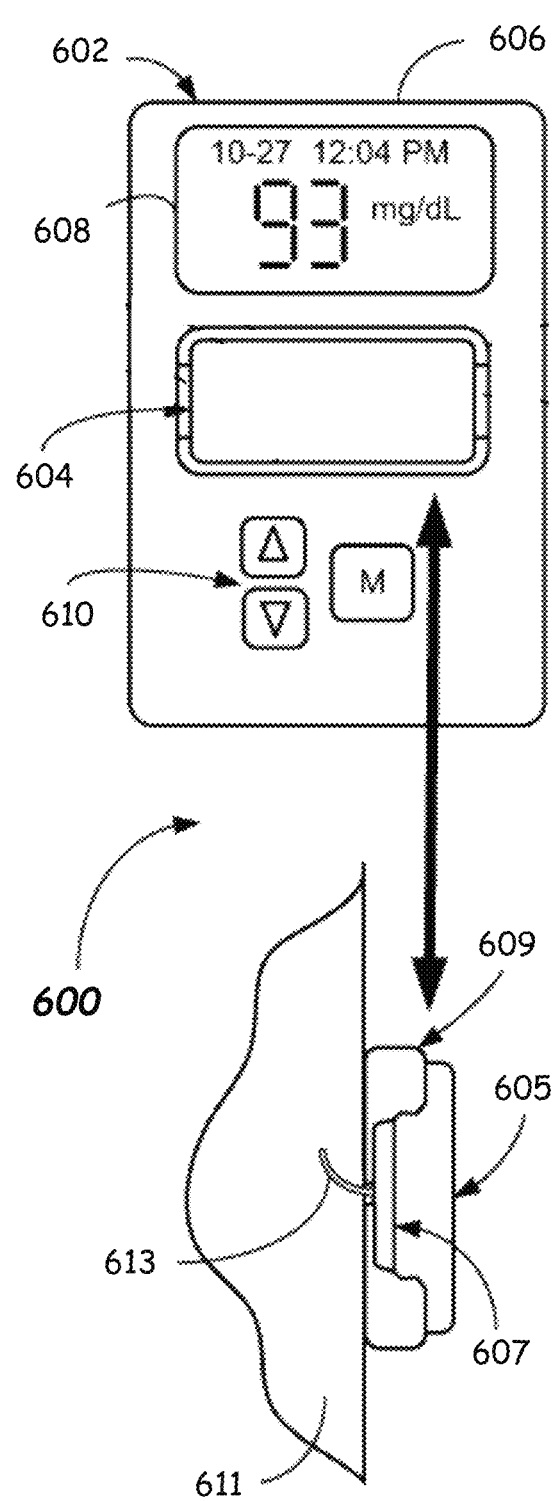
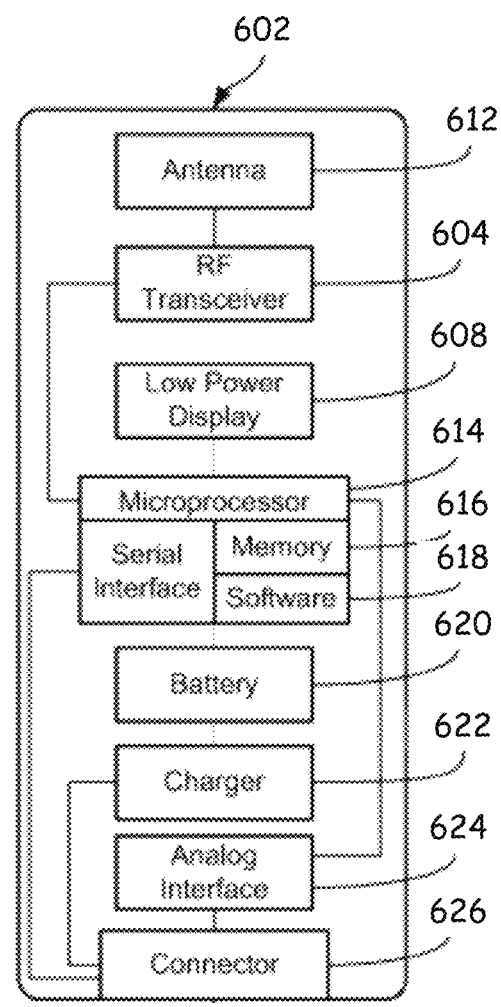
FIG. 6A
FIG. 6B

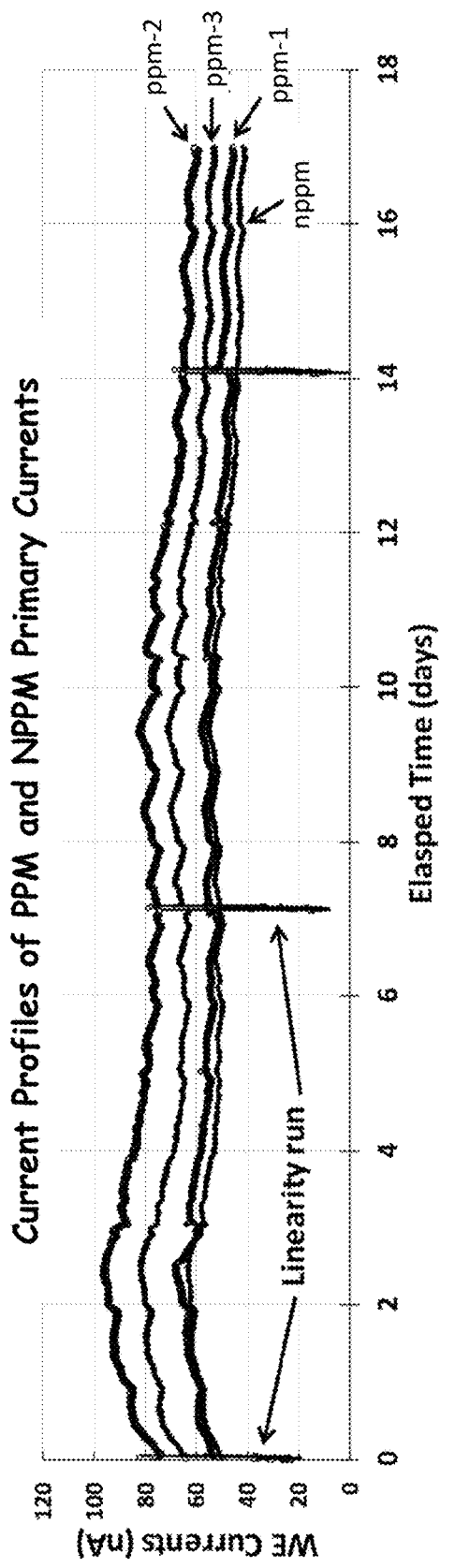
FIG. 12A
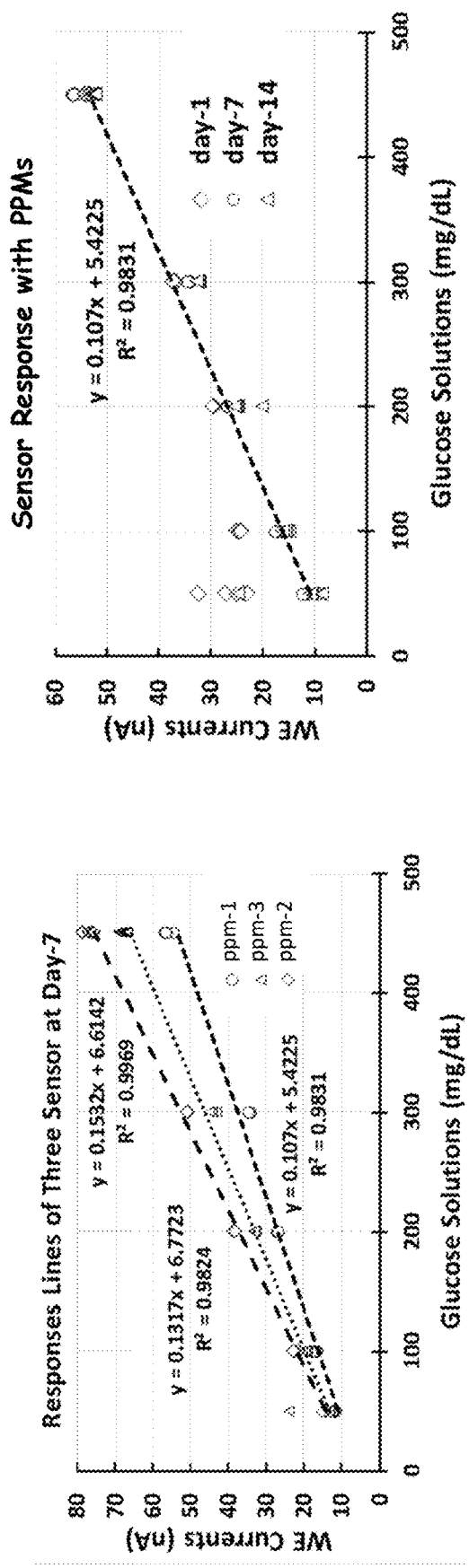
FIG. 12B
FIG. 12C

APPARATUS AND METHODS OF PROBING SENSOR OPERATION AND/OR DETERMINING ANALYTE VALUES DURING CONTINUOUS ANALYTE SENSING

The present application claims priority to U.S. Provisional Patent Application No. 62/801,592, filed Feb. 5, 2019, and titled "APPARATUS AND METHODS FOR PROBING SENSOR OPERATION OF CONTINUOUS ANALYTE SENSING AND AUTO-CALIBRATION" which is hereby incorporated by reference herein in its entirety.

FIELD

This disclosure relates to continuous sensor monitoring of an analyte in a bodily fluid.

BACKGROUND

Continuous analyte sensing in an in-vivo or in-vitro sample, such as, e.g., continuous glucose monitoring (CGM), has become a routine sensing operation in the field of medical devices, and more specifically, in diabetes care. For biosensors that measure analytes in a whole blood sample with discrete sensing, such as, e.g., pricking a finger to obtain a blood sample, the sample's temperature and hematocrit of the blood sample may be major sources of error. However, for sensors deployed in a non-whole blood environment with relatively constant temperatures, such as sensors used in a continuous in-vivo sensing operation, other sensor error sources may exist.

Accordingly, improved apparatus and methods of in-situ calibration of CGM sensors are desired.

SUMMARY

According to aspects of the disclosure, apparatus and methods are provided that may probe a sensor with respect to its sensitivity or operating conditions, extract sensitivity indices for the sensor's operating conditions, and provide an in-situ calibration other than the factory calibration as needed.

In some embodiments, a method of compensating for errors during continuous glucose monitoring (CGM) measurements is provided that includes providing a CGM device including a sensor, a memory and a processor; applying a constant voltage potential to the sensor, measuring primary current signals resulting from the constant voltage potential and storing measured primary current signals in the memory; between measurements of primary current signals, applying a probing potential modulation sequence to the sensor, measuring probing potential modulation current signals resulting from the probing potential modulation sequence and storing measured probing potential modulation current signals in the memory; and for each primary current signal, employing the primary current signal and a plurality of the measured probing potential modulation current signals associated with the primary current signal to determine a glucose value.

In some embodiments, a method of making a continuous glucose monitoring (CGM) device is provided that includes creating a prediction equation based on a plurality of probing potential modulation current signals measured for a reference CGM sensor in response to a probing potential modulation sequence applied to the reference CGM sensor before or after primary current signals are measured for the reference CGM sensor; providing a CGM device including a sensor, a memory and a processor; storing the prediction equation in the memory of the CGM device; storing computer program code in the memory of the CGM device that, when executed by the processor, causes the CGM device to (a) apply a constant voltage potential to the sensor, measure primary current signals resulting from the constant voltage potential and store measured primary current signals in the memory; (b) between measurements of primary current signals, apply a probing potential modulation sequence to the sensor, measure probing potential modulation current signals resulting from the probing potential modulation sequence and store measured probing potential modulation current signals in the memory; (c) for each primary current signal, employ the primary current signal, a plurality of the measured probing potential modulation current signals associated with the primary current signal and the stored prediction equation to determine a glucose value; and (d) communicate determined glucose values to a user of the CGM device.

In some embodiments, a continuous glucose monitoring (CGM) device is provided that includes a wearable portion having a sensor configured to produce current signals from interstitial fluid; a processor; a memory coupled to the processor; and transmitter circuitry coupled to the processor. The memory includes a prediction equation based on primary current signals generated by application of a constant voltage potential applied to a reference sensor, and a plurality of probing potential modulation current signals generated by application of a probing potential modulation sequence applied between primary current signal measurements. The memory also includes computer program code stored therein that, when executed by the processor, causes the CGM device to (a) measure and store a primary current signal using the sensor and memory of the wearable portion; (b) measure and store a plurality of probing potential modulation current signals associated with the primary current signal; (c) employ the primary current signal, the plurality of probing potential modulation current signals and the stored prediction equation to compute a glucose value; and (d) communicate the glucose value to a user of the CGM device.

In some embodiments, a method of determining analyte concentrations during continuous monitoring measurements is provided that includes inserting a biosensor subcutaneously into a subject, the biosensor including a counter electrode, a reference electrode and a working electrode having a chemical composition configured to oxidize a point-of-interest analyte; applying a constant voltage to the working electrode having the chemical composition so as to generate a continuous current flow from the working electrode; sensing and storing primary current signals from the working electrode into a memory; after sensing each primary current signal, applying a probing potential modulation sequence to the working electrode, and sensing and storing probing potential modulation currents generated in response to the probing potential modulation sequence into the memory; gathering a primary current signal and probing potential modulation currents generated after the primary current signal; and employing the gathered primary current signal and probing potential modulation currents to compute an analyte value.

In some embodiments, a method of probing a condition of a continuous analyte monitoring (CAM) sensor and of calibrating the sensor based thereon is provided that includes applying an operating voltage to the CAM sensor; probing a condition of the CAM sensor by applying at least one voltage step greater than the operating voltage and at least one voltage step less than the operating voltage; measuring output currents of the CAM sensor in response to the probing; calculating calibration indices via ratios of the output currents; and calibrating the CAM sensor based on the calibration indices.

In some embodiments, a continuous analyte monitoring (CAM) sensor apparatus is provided that includes a management unit including a wireless transmitter/receiver in communication with a wireless transmitter coupled to an on-body sensor, the management unit further comprising a processor, a memory, and software, wherein the processor and software are operative to (a) apply an operating voltage to the on-body sensor; (b) probe a condition of the on-body sensor by applying at least one voltage step greater than the operating voltage and at least one voltage step less than the operating voltage; (c) measure output currents of the on-body sensor in response to the probing; (d) calculate calibration indices via ratios of the output currents; and (e) calibrate the on-body sensor based on the calibration indices.

In some embodiments, a method of applying probing potential modulation during continuous analyte monitoring for determination of analyte concentration is provided that includes applying a constant operating voltage to an analyte sensor during a continuous sensor operation; applying at least one probing potential modulation step different than the constant operating voltage in each cycle of the continuous sensor operation; measuring primary current from the constant operating voltage in each cycle and at least one companion probing potential modulation current in each cycle, responsive to analyte concentration; and determining analyte concentration from the primary current and the at least one companion probing potential modulation current from the at least one probing potential modulation step.

In some embodiments, a continuous analyte monitoring (CAM) device is provided that includes a wearable portion having a sensor configured to be subcutaneously inserted into a subject and to produce current signals from interstitial fluid; a processor; and a memory coupled to the processor. The memory includes computer program code stored therein that, when executed by the processor, causes the CAM device to: (a) apply a constant voltage to the sensor so as to generate a primary current flow from the sensor; (b) sense and store primary current signals generated in response to the constant voltage into the memory; (c) between sensing primary current signals, apply a probing potential modulation sequence to the sensor, and sense and store probing potential modulation currents generated in response to the probing potential modulation sequence into the memory; and (d) employ primary current signals and probing potential modulation currents to compute analyte values over a time period of at least a week. The CAM device does not employ an in-situ calibration during the time period.

Still other aspects, features, and advantages in accordance with these and other embodiments of the disclosure may be readily apparent from the following detailed description, the appended claims, and the accompanying drawings. Accordingly, the drawings and descriptions herein are to be regarded as illustrative in nature, and not as restrictive.

BRIEF DESCRIPTION OF THE DRAWINGS

The drawings, described below, are for illustrative purposes and are not necessarily drawn to scale. The drawings are not intended to limit the scope of the disclosure in any way.

FIGS. 6A and 6B illustrate block diagrams of CGM sensor apparatus according to one or more embodiments.

FIGS. 7B, 7C, 7D, 7E and 7F illustrate example sequences of probing potential modulations that may be employed in accordance with embodiments provided herein, wherein FIG. 7B illustrates step-wise probing potential modulations, FIG. 7C illustrates one step down/up probing potential modulations in two back-to-back sequences, FIG. 7D illustrates asymmetrical step probing potential modulations, FIG. 7E illustrates linear scan/triangle probing potential modulations and FIG. 7F illustrates a one-step potential modulation followed by a direct step returning to a constant operating potential.

FIG. 12A illustrates a graph of working electrode current versus elapsed time for three sensors subjected to probing potential modulations (sensor ppm-1, ppm-2 and ppm-3) and one sensor subjected to no probing potential modulations (sensor nppm-1) in accordance with embodiments provided herein.

FIG. 12B illustrates working electrode current versus glucose concentration for three sensors (ppm-1, ppm-2, ppm-3) at day-7 in accordance with embodiments provided herein.

FIG. 12C illustrates working electrode current versus glucose concentration for one sensor (sensor ppm-1) at day-1, day-7 and day-14 in accordance with embodiments provided herein.

DETAILED DESCRIPTION

Figure 1:
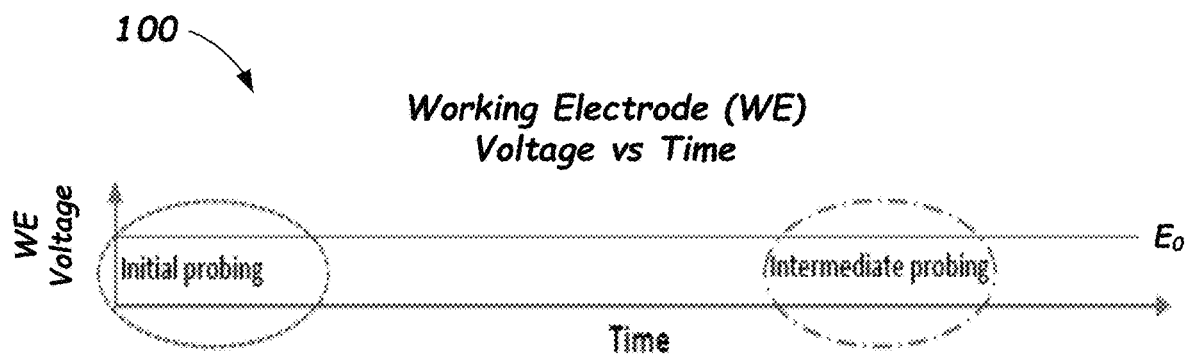
FIG. 1 illustrates a graph of applied voltage $E_0$ for a continuous glucose monitoring (CGM) sensor versus time according to one or more embodiments of the disclosure.

Reference will now be made in detail to example embodiments of the disclosure, which are illustrated in the accompanying drawings. Wherever possible, the same reference numbers will be used throughout the drawings to refer to the same or like parts. Features of the various embodiments described herein may be combined with each other, unless specifically noted otherwise.

The terms "voltage," "potential" and "voltage potential" are used interchangeably. "Currents," "signals" and "current signals" are also used interchangeably, as are "continuous analyte monitoring" and "continuous analyte sensing." As used herein, probing potential modulations refer to intentional changes made periodically to the otherwise constant voltage potential applied to a sensor during continuous analyte sensing, such as application of probing potential steps, pulses, or other potential modulations to the sensor. Primary data points or primary currents refer to measurements of current signals generated in response to an analyte at a constant voltage potential applied to a sensor during continuous analyte sensing. Probing potential modulation (ppm) currents refer to measurements of current signals generated in response to probing potential modulations applied to the sensor during continuous analyte sensing. Reference sensors refer to sensors used to generate primary data points and ppm currents in response to reference glucose concentrations represented by BGM readings, for example (e.g., primary currents and ppm currents measured for the purpose of determining prediction equations that are subsequently stored in a continuous analyte monitoring (CAM) device and used during continuous analyte sensing to determine analyte concentrations).

For sensors deployed in a non-whole blood environment with relatively constant temperatures, such as sensors used in a continuous in-vivo sensing operation, sensor error may be related to the sensor's short and long-term sensitivity and method of calibration thereafter. There are several problems/issues associated with such a continuous sensing operation: (1) the long break-in (warmup) time, (2) the factory or in-situ calibration, and (3) the change of sensitivity during the continuous sensing operation. These issues/problems are seemingly related to the sensor sensitivity as expressed in the initial decay (break-in/warmup time), the change of sensitivity due to the susceptibility of the sensor to the environment while in sensor production, and the environments/conditions in which the sensor is thereafter deployed.

According to one or more embodiments of the disclosure, apparatus and methods are operative to probe an initial starting condition of a continuous sensor operation for a sample analyte and to probe the sensor condition at any point thereafter during the sensor's continuous sensing operation. The results of the probing sequence may include calibration indices, determined from electrical signals obtained from the probing sequence, that indicate whether in-situ adjustment of the sensor's calibration either initially and/or at random check points is needed. In some embodiments, the output of the probing method and its calibration indices may provide the in-situ calibration internally for the continuous sensor operation (and/or in embodiments described below, the probing method may reduce and/or eliminate the need for in-situ calibrations).

Embodiments described herein include systems and methods for applying probing potential modulations on top of the otherwise constant voltage applied to an analyte sensor. The terms voltage, potential, and voltage potential are used herein interchangeably.

Methods are provided of formulating parameters for a prediction equation that may be employed to accurately determine analyte concentrations continuously from an analyte sensor. Furthermore, a method of and apparatus for determining analyte concentrations are provided with the use of probing potential modulation (ppm) self-sufficient signals (e.g., working electrode currents resulting from the application of probing potential modulations). Such methods and apparatus may allow analyte concentration determinations while (1) overcoming the effects of different background interfering signals, (2) levelling or removing the effects of different sensor sensitivities, (3) shortening the warmup time at the beginning of a (long-term) continuous monitoring process, (4) correcting sensor sensitivity changes over the continuous monitoring process, and/or (5) correcting the effects of temperature on sensor output currents. These and other embodiments are described below with reference to FIGS. 1-20.

For a continuous glucose monitoring (CGM) biosensor, which is usually operated with a constant applied voltage, the currents from the mediator are measured continuously as a result of the enzyme oxidation of the target analyte glucose. In practice, currents are typically measured or sensed every 3 to 15 minutes or at another regular interval despite being referred to as continuous. There is an initial break-in time when the CGM sensor is first inserted/implanted into a user, which may last from 30 minutes to several hours. Once the CGM sensor is broken-in, its sensitivity may still change for various reasons. Thus, there is a need to sense the sensor's operating condition during its initial and after break-in times to identify any changes in its sensitivity.

Figure 2:
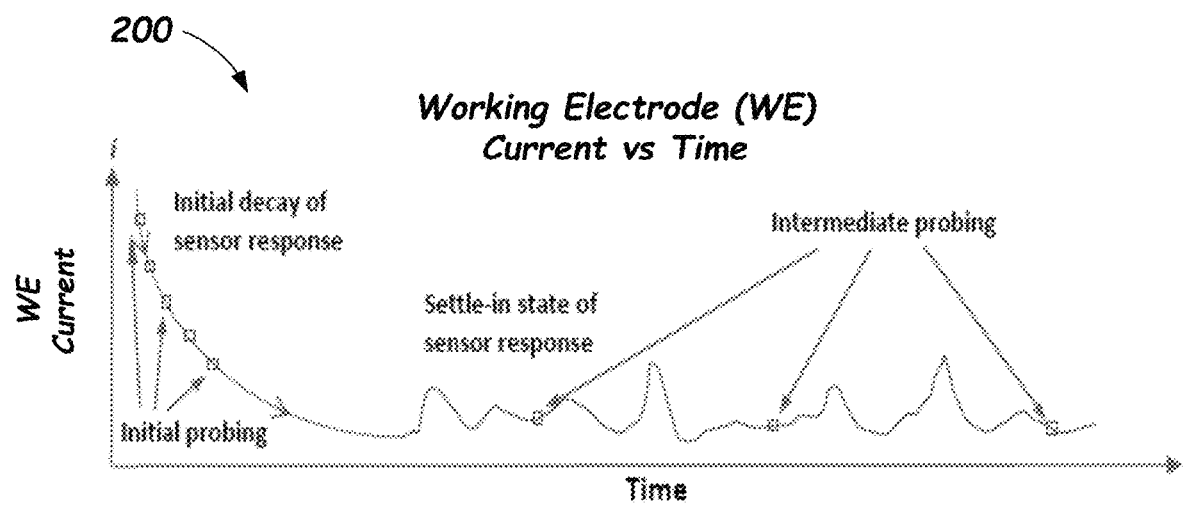
FIG. 2 illustrates a graph of a CGM sensor's output current versus time according to one or more embodiments of the disclosure.
Figure 3:
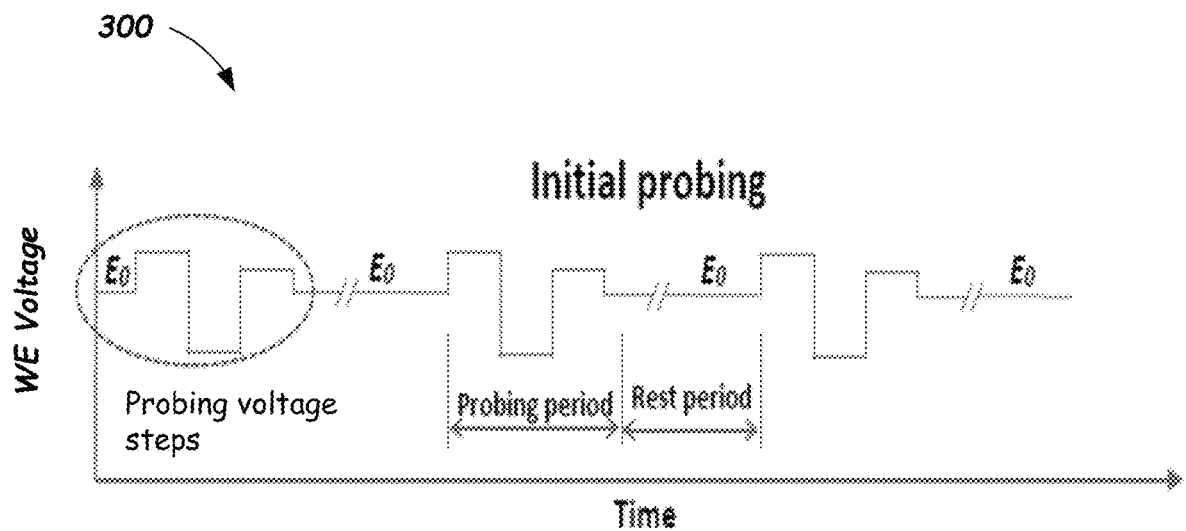
FIG. 3 illustrates a graph of varying CGM sensor input potential modulation steps versus time during an initial probing period according to one or more embodiments of the disclosure.
Figure 4:
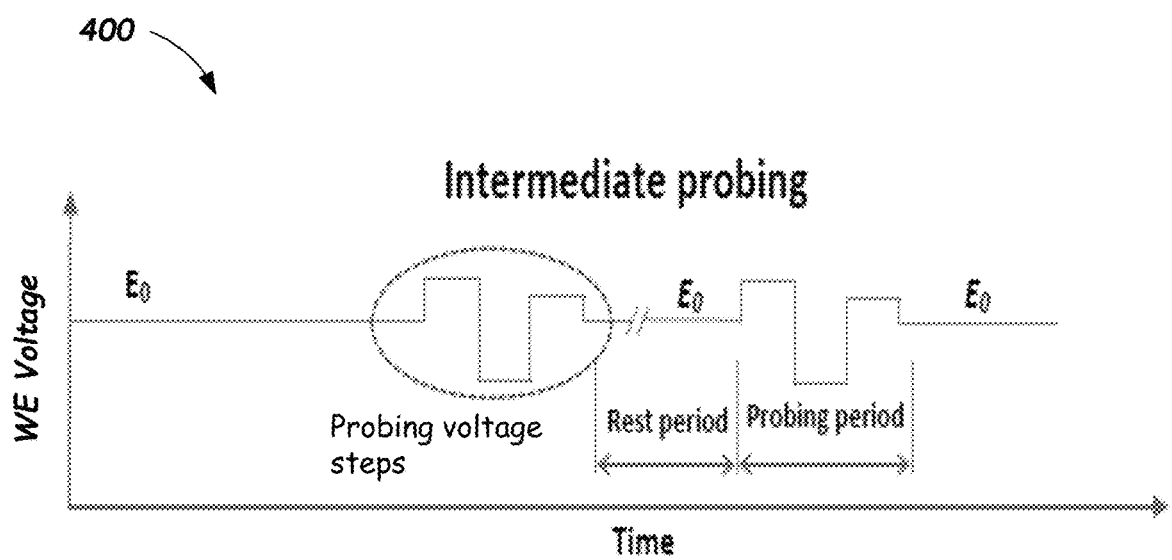
FIG. 4 illustrates a graph of varying CGM sensor input potential modulation steps versus time during an intermediate probing period according to one or more embodiments of the disclosure.

The CGM sensor operation starts with the applied voltage $E_0$ after it is inserted/implanted subcutaneously into a user. The applied voltage $E_0$ is usually at a point on the redox plateau of the mediator. For the natural mediator of oxygen with the enzyme of glucose oxidase, the oxidation plateau of hydrogen peroxide $H_2O_2$ (the oxidation product of the enzyme reaction) ranges from about 0.5 to 0.8 volts versus an Ag/AgCl reference electrode in a media of about 100-150 mM chloride concentration. The operation potential for the glucose sensor may be set at 0.55-0.7 volts, which is within the plateau region. FIG. 1 shows such a fixed potential (applied voltage) $E_0$, while FIG. 2 shows the typical behavior of the sensor's output currents at the initial state with decay and the settle-in state, wherein the sensor records the up/down changes of the glucose during the deployment. Specifically, FIG. 1 illustrates a graph 100 of working electrode voltage versus time during a continuous sensing operation, while FIG. 2 illustrates a graph 200 of working electrode current versus time.

FIG. 1 also shows the positions in time for the initial probing and the intermediate probing using the probing potential modulations. Example probing potential modulations are further illustrated in FIGS. 3 and 4. The probing potential modulations and their adjacent cluster potential steps may be further defined as follows:

Probing potentials: For the initial probing of the sensor condition/environment, in some embodiments, probing may start 0-5 minutes after sensor insertion and the initial applied voltage. Other initial probing start times may be used. In some embodiments, the probing potential modulations may include at least one forward potential step from the base potential $E_0$. That is, the forward step potential $E_1$ is higher than $E_0$ with $\Delta E_{1,0} = E_1 - E_0 > 0$ and in the order of 0.05-0.3 volts. The probing potential modulations also may include at least one reverse potential step $E_2$ such that $\Delta E_{2,0} = E_2 - E_0$ is in the order of −0.05 to −0.5 volts; that is, $E_2$ is substantially lower than $E_1$ and $E_0$, where $\Delta E_{2,1} = E_2 - E_1 < 0$ and $\Delta E_{2,0} = E_2 - E_0 < 0$.

Figure 5A:
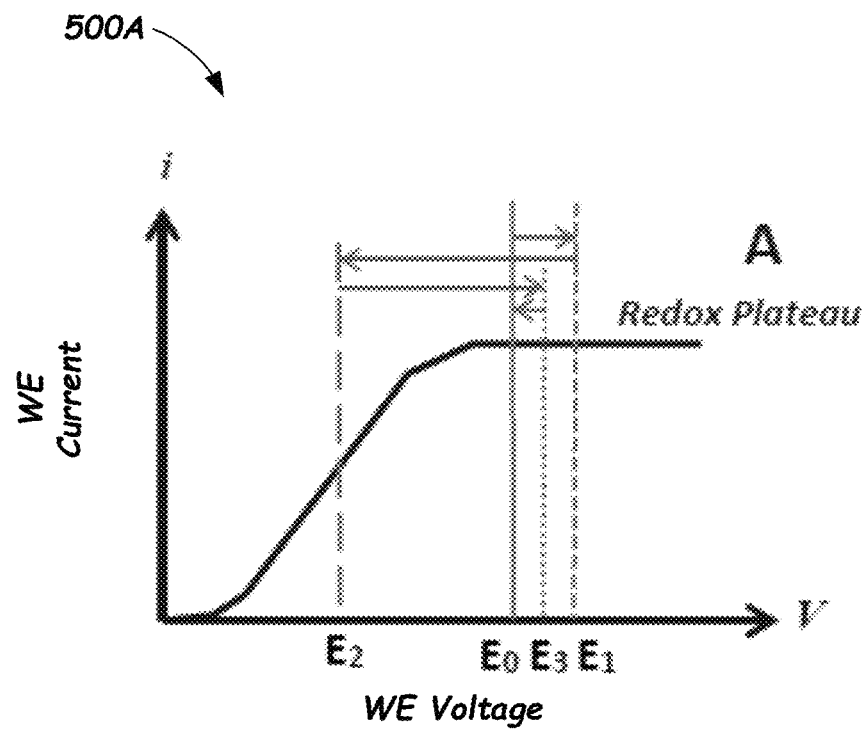
FIG. 5A illustrates a graph of a current-voltage relationship at and near a redox plateau for a redox species (mediator) according to one or more embodiments of the disclosure.
Figure 5B:
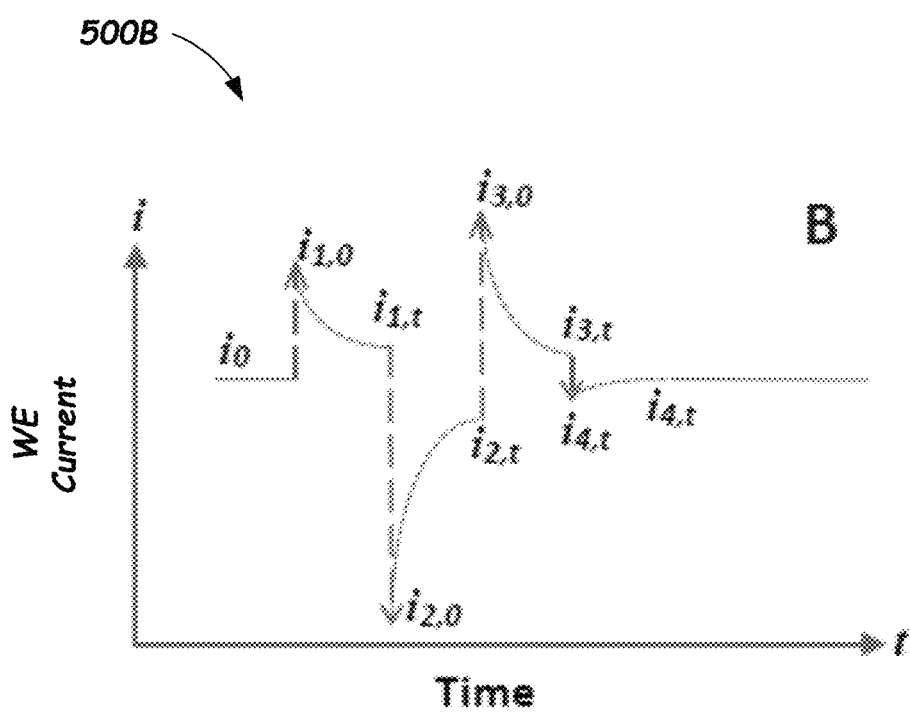
FIG. 5B illustrates a graph of a typical current-time relationship for the currents before, during, and after the probing potential modulations shown in FIGS. 3 and 4 according to one or more embodiments of the disclosure.

FIGS. 5A and 5B illustrate example relative potential steps (graph 500A) and the typical current behaviors (graph 500B) during the back/forth potential steps described above. The potential $E_2$ is designed to set the mediator in a partial reduced state. The ratio of the potential step ending currents $i_{1,t}/i_{2,t}$ may provide an assessment of the sensor condition and sensitivity. That is, $i_{1,t}$ ($i_{0,t}$, $i_{3,t}$ as well) provides the diffusion limited current from the oxidizing of the reduced state of the mediator, while $i_{2,t}$ provides the kinetic current which is related to the sensor sensitivity. Additional potential steps may include a forward potential step $E_3$ higher than or equal to $E_0$, but lower than $E_1$, and another reverse potential step to return to $E_0$ from $E_3$. This probing potential sequence is designed to have a minimal perturbation to the on-going current monitoring at a fixed potential $E_0$ after the final probing potential step returns to $E_0$. After the probing potential modulations, the regular current record frequency may resume.

Probing period and rest period: In some embodiments, the timing of one probing sequence including the multiple probing potential modulations (potential steps in this example) may be in an order of 5-100 seconds where each potential step may have a duration of 1-20 seconds with equal or unequal step size for the individual steps. This one probing period may be separated by a rest period of 1-30 minutes, for example. An example of such a probing scheme may be represented by a probing period of 30 sec for a probing group of 3-5 steps, separated by a rest period of 14.5 minutes, with one probing cycle being in 15 minutes. While the long-term sensor response currents may be measured at a frequency of every 1-15 minutes, the current sampling interval of the probing potential modulations may be in the order of 0.1-5 sec, depending on the step duration of the probing potential modulations.

Current decay constant of the probing potential modulations: Example probing potential modulations positions and their typical current decay behavior within their potential steps are shown in FIGS. 5A and 5B. The probing potential modulation (PPM) currents are, in general, proportional to the magnitude of the step potential by:

$$i = \frac{\Delta E}{R_S} e^{-t/R_S C_d} \quad (1)$$

where $\Delta E$ is the potential step; $R_S$ is the solution resistance between the working electrode and the reference electrode or the combined reference/counter electrode; $C_d$ is electrode surface capacitance; and t is the time after the initial step potential. After the initial current spike characterized by $\Delta E/R_S$, the current will decay approximately exponentially ($\exp(-t/R_S C_d)$). Thus, if $\Delta E > 0$, the step potential current will be positive and if $\Delta E < 0$, the step potential current will be negative. Such behaviors are depicted in FIG. 5B for the four potential steps. For each probing potential modulation, there is a decay characteristic of the sensor electrode, the enzyme/membrane encapsulation and the sensor's environment. This decay may be characterized by the decay constant:

$$K_p = \frac{ln i_{n,o} - ln i_{n,t}}{ln t_{n,o} - ln t_{n,t}} \quad (2)$$

where $i_{n,0}$ denotes the initial current of a step at $E_n$ (n=1, 2, 3, . . . ) and $i_{n,t}$ denotes the ending current of a step at time t for each potential step. It may also be defined by the ratios of $i_{1,t}/i_{1,0}$, $i_{2,t}/i_{2,0}$, $i_{3,t}/i_{3,0}$, and $i_{4,t}/i_{4,0}$, where $i_{n,0}$ is the initial step current and $i_{n,t}$ is the ending step current at time t of each potential step. These decay constants may reflect the sensor sensitivity changes, or the sensor's enzyme/membrane condition changes during the break-in time.

Ratios of the potential step ending currents: The potential step ending currents from $E_0$, $E_1$, and $E_3$ should be close to each other after sufficient decay of the currents. This occurs because $E_0$, $E_1$, and $E_3$ are at the redox plateau with the diffusion limited current. However, the potential step ending current for $E_2$ may be substantially smaller than those from $E_0$, $E_1$, and $E_3$, because $E_2$ is in a region with current much lower than that of the diffusion limited currents in the redox plateau. In particular, the ratio of $i_{1,t}/i_{2,t}$ may indicate the relative sensitivity of the sensor at the nearby time, and so may $i_{3,t}/i_{2,t}$. Comparison of these ratios to the average ratios of $i_{1,t}/i_{2,t}$ and $i_{3,t}/i_{2,t}$ from the factory calibration may provide the relative sensitivity of the sensor and thus the basis for an in-situ calibration. This ratio may also provide the sensor conditions at various stages. Accordingly, the factory calibration may be based not only on the response curve for the sensor (e.g., calibration constant sets of slope and intercept, the coefficients of a polynomial equation that relates sensor current signals and analyte concentrations, etc.), but also based on the calibration indices obtained from probing potential modulations. While the calibration constants of slope and intercept may only be obtained with in-vitro dosing of reference concentrations of the analyte, the calibration indices described herein may be generated through in-situ potential modulation (or other types of probing potential modulations) with potential steps higher and lower the operation potential $E_0$, which are added as additional calibration elements to the factory calibration. For example, in some embodiments, calibration constants may include multiple sets of slope and intercept, and calibration indices may be correlated with the different sets of slope and intercept. These constants and indices may be stored in the sensor system's memory for in-situ calibration during the sensor operation.

Initial probing: If a probing scheme is applied every 15 minutes, and while returning to the normal applied voltage $E_0$ afterwards, the first hour will provide four different sets of indices characteristic of the sensor, where different calibration constants may be applied to predict the glucose concentrations within such a short period. As probing indices generated from the four consecutive probing potential modulations change along the break-in time, a trend for the initial decay currents may be established to predict the following current behavior and thus provide the glucose determination based on the trending of the probing indices and the factory calibration constants, even when the general current behavior is still decaying. This approach may help to shorten the overall sensor break-in/warmup time from about 3 hours to 1 hour in some embodiments. Initial probing may be performed at other time periods (e.g., time periods less than every 15 minutes or greater than every 15 minutes so that fewer or more than four different sets of indices characteristic of the sensor may be obtained).

Intermediate probing: In some embodiments, the probing potential modulations may be applied periodically on a daily basis to provide an anchor to the long-term monitoring currents. For example, one or more sets of probing potential modulations may be applied when the sensor is at a relatively low variation state. When the probing indices generated from the probing potential modulations show a change in the sensor sensitivity, sensitivity adjustments may be applied to correct for the change. This is a step of in-situ calibration (internal calibration).

Sensor system intelligence: The probing potential modulations scheme may be applied as a routine such as initially, or may be applied periodically. The application of probing potential modulations may employ some built-in intelligence (e.g., software operating on a microprocessor of a management unit of a CGM sensor) for initiating the potential modulations and performing the calculations of the indices to be used for in-situ sensor calibration.

FIGS. 6A and 6B illustrate CGM apparatus 600 according to one or more embodiments. CGM apparatus 600 includes a management unit 602 that has a wireless transmitter/receiver unit 604, a wireless transmitter 605 coupled to an on-body sensor 607, which is received in a sensor pod 609 mountable to a user's body 611 (e.g., torso). Wireless transmitter 605 communicates sensor readings and other data to wireless transmitter/receiver unit 604. A cannula, needle, or sensor component 613 (e.g., an analyte sensor) is inserted into the user's body 611 through known means, such as use of an insertion set and interfaces with the on-body sensor 607 to allow substantially continuous sensing of a glucose level in the user's interstitial fluid. The management unit 602 has a housing 606, a display screen 608 that displays glucose readings and/or trends, and a user interface 610 that may include a plurality of buttons for controlling various features of the management unit 602. As shown in FIG. 6B, management unit 602 also includes an antenna 612, a processor 614 (which may be, e.g., a microprocessor), a memory 616, software 618, a rechargeable battery 620, a battery charger 622, an analog interface 624, and a cable connector 626. The processor 614, memory 616, and software 618 are operative to perform the probing of a CGM sensor (e.g., on-body sensor 607) with respect to its sensitivity or operating conditions, the extracting and storing of sensitivity indices for the CGM sensor's operating conditions, and the in-situ calibration adjustment as needed of CGM apparatus 600 as described above.

Embodiments described herein employ probing potential modulations as periodic perturbations to the otherwise constant voltage potential applied to the working electrode of a subcutaneous biosensor in a continuous sensing operation (e.g., for monitoring biological sample analyte such as glucose). While the previous embodiments describe use of probing potential modulations during an initial time period after insertion of a sensor, and at intermediate time periods, probing potential modulations may be used at other time periods. For example, during a continuous sensing operation, such as continuous glucose monitoring, sensor working electrode current is typically sampled every 3-15 minutes (or at some other frequency) for glucose value determinations. These current measurements represent the primary currents and/or primary data points used for analyte determinations during continuous sensing operation. In some embodiments, periodic cycles of probing potential modulations may be employed after each primary current measurement so that a group of self-sufficient currents accompanies each primary data point with information about the sensor/electrode status and/or condition.

Probing potential modulations may include one or more steps in potential that are different than the constant voltage potential normally used during continuous analyte monitoring. For example, probing potential modulations may include a first potential step above or below the constant voltage potential, a first potential step above or below the constant voltage potential and then a potential step returning to the constant voltage potential, a series of potential steps above and/or below the constant voltage potential, voltage steps, voltage pulses, pulses of the same or different durations, square waves, sine waves, triangular waves, or any other potential modulations.

As described, conventional biosensors used in continuous analyte sensing are operated by applying a constant potential to the working electrode (WE) of the sensor. Under this condition, the currents from the WE are recorded periodically (e.g., every 3-15 minutes or at some other time interval). In this way, biosensors generate currents that are only attributable to changes in analyte concentrations, not changes in applied potential. That is, non-steady-state currents associated with the application of different potentials are not present. While this approach simplifies the continuous sensing operation, the current signals in the data stream from application of a constant potential to the sensor provide minimum information about the sensor status/condition. That is, sensor current signals from application of a constant potential to a sensor provide little information relevant to issues associated with long-term continuous monitoring by the sensor, such as lot-to-lot sensitivity variations, the long warmup time due to initial signal decay, sensor sensitivity changes over a long-term monitoring process, effects from varying background interfering signals, or the like.

Embodiments described herein include systems and methods for applying probing potential modulations on top of the otherwise constant voltage applied to an analyte sensor. Methods are provided for formulating parameters for a prediction equation that may be employed to accurately determine analyte concentrations continuously from an analyte sensor. Furthermore, methods of and systems for determining analyte concentrations with the use of probing potential modulation (ppm) self-sufficient signals are provided. Such methods and systems may allow analyte concentration determinations while (1) overcoming the effects of different background interfering signals, (2) levelling or removing the effects of different sensor sensitivities, (3) shortening the warmup time at the beginning of a (long-term) continuous monitoring process, (4) correcting sensor sensitivity changes over the continuous monitoring process, and/or (5) correcting the effects of temperature on sensor output currents. These and other embodiments are described below with reference to FIGS. 7A-19.

Figure 7A:
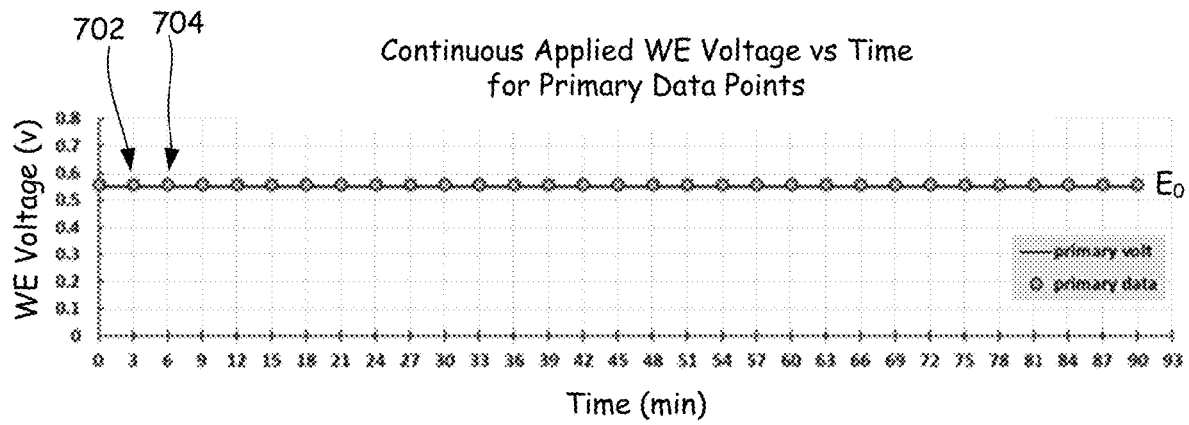
FIG. 7A illustrates a graph of applied voltage $E_0$ for a continuous glucose monitoring (CGM) sensor versus time according to one or more embodiments of the disclosure.

FIG. 7A illustrates a graph of applied voltage $E_0$ for a continuous glucose monitoring (CGM) sensor versus time according to one or more embodiments of the disclosure. Example times at which measurements of primary data points may be made, and subsequent probing potential modulations may be applied, are shown. As shown in FIG. 7A, the constant voltage potential $E_0$ applied to the working electrode of an analyte sensor may be about 0.55 volts in this example. Other voltage potentials may be used. FIG. 7A shows an example of a typical cycle of the primary data points taken at a constant applied voltage. Primary data points are the data points measured or sampled at a constant applied voltage and at regular intervals, such as 3-15 minutes, during continuous glucose monitoring and used to compute glucose values for a user. Primary data points may be working electrode currents measured for an analyte sensor during continuous analyte monitoring, for example. FIG. 7A does not show primary data points, but the time and voltage at which each primary data point is measured. For example, circle 702 in FIG. 7A represents the time/voltage (3 minutes/0.55 volts) at which a first primary data point (e.g., a first working electrode current) is measured for a sensor biased at a voltage of $E_0$. Likewise, circle 704 in FIG. 7A represents the time/voltage (6 minutes/0.55 volts) at which a second primary data point (e.g., second working electrode current) is measured for a sensor biased at a voltage of $E_0$.

Figure 7B:
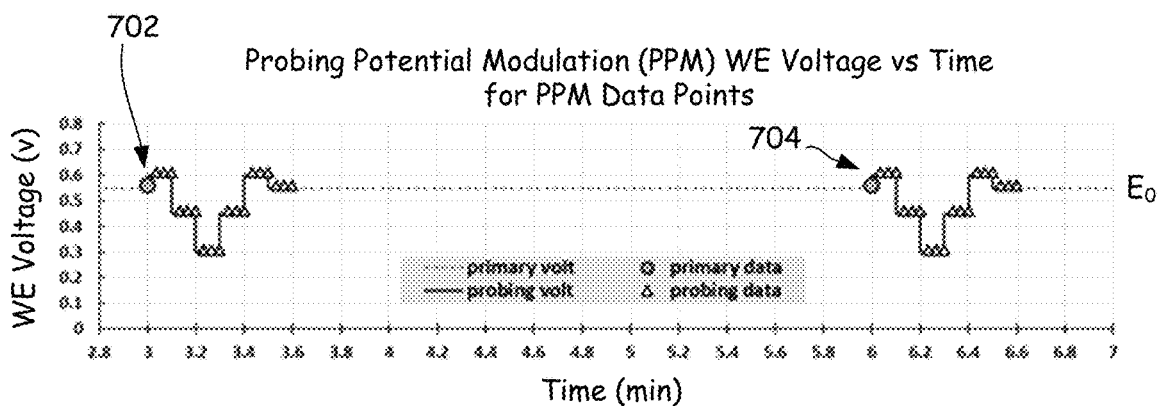
Figure 7C:
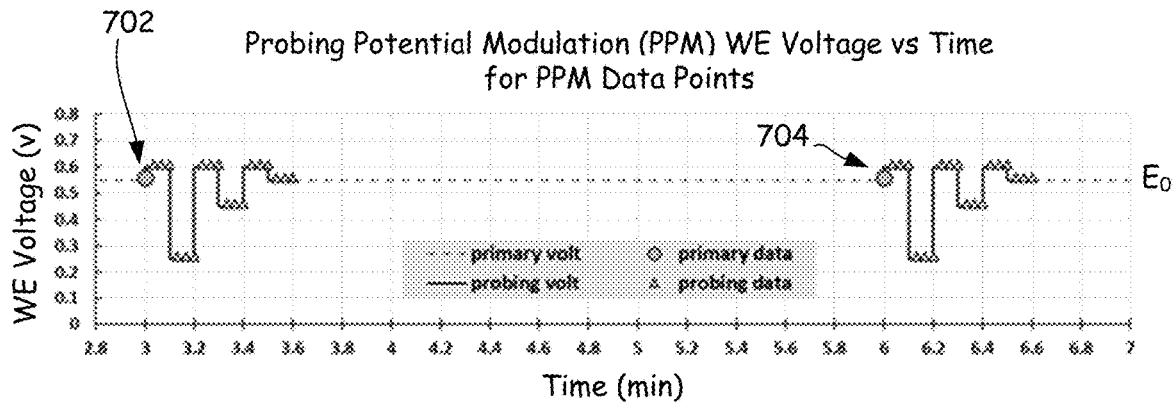
Figure 7D:
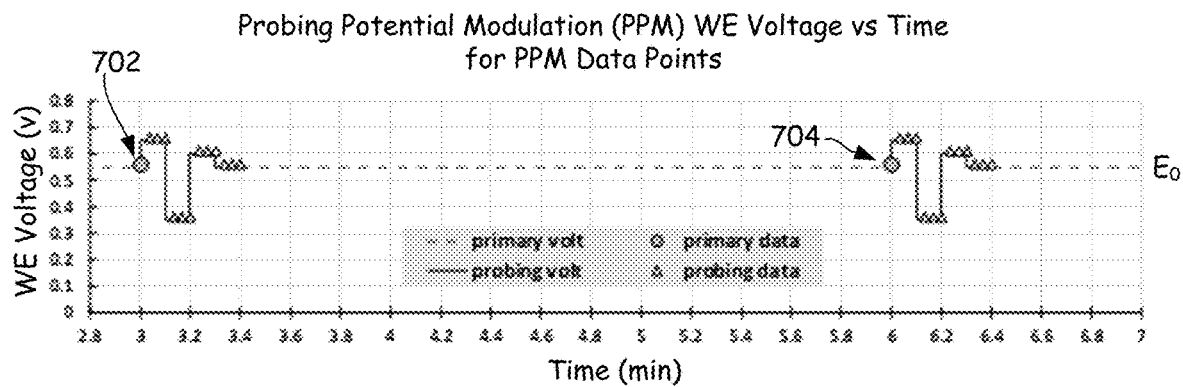
Figure 7E:
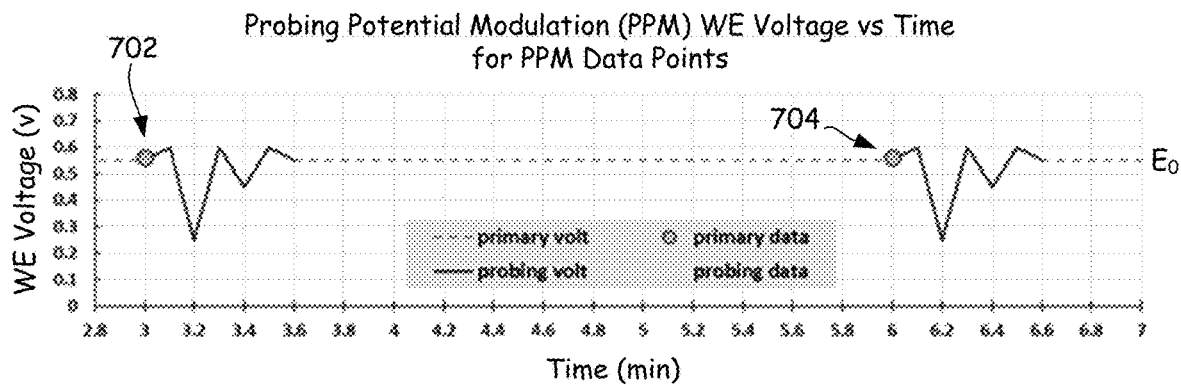
Figure 7F:
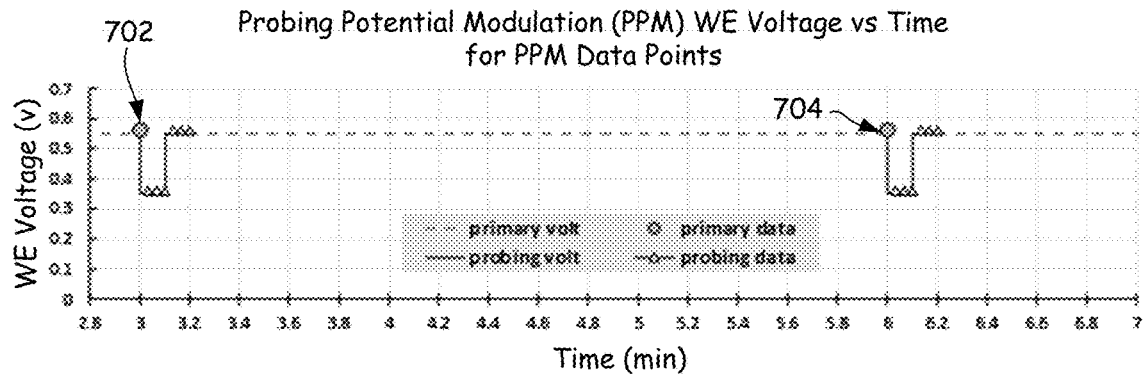

FIGS. 7B, 7C, 7D, 7E and 7F illustrate example sequences of probing potential modulations that may be employed in accordance with embodiments provided herein. The triangles on top of the potential profiles denote the times at which probing potential modulation currents are measured, as examples in this embodiment. For example, FIG. 7B illustrates step-wise probing potential modulations, FIG. 7C illustrates one step down/up probing potential modulations in two back-to-back sequences, FIG. 7D illustrates asymmetrical step probing potential modulations, FIG. 7E illustrates linear scan/triangle probing potential modulations, and FIG. 7F illustrates a one-step potential modulation followed by a direct step returning to the constant operating potential, respectively. Other probing potential modulations types may be used. In these figures, "primary volt" denotes the constant applied potential under the normal sensor operation; "primary data" denotes the timing of the primary data points (e.g., current signals) recorded periodically as being indicative of the analyte concentration; "probing volt" denotes the probing potential modulation potentials applied as perturbation to the primary/constant applied potential; and "probing data" denotes the timing of the current signals generated by probing potential modulations and recorded at a specified sampling rate. While FIGS. 7B-7E illustrate probing potential modulations of 4 or more steps, it will be understood that few or more probing potential modulation steps may be used (e.g., 1, 2, 3, 4, 5, 6, 7, 8, etc.).

Probing potential modulations may be applied before or after primary data points are measured. In the embodiments of FIGS. 7B-7E, probing potential modulations are applied to a sensor immediately after each primary data point is measured (e.g., after a primary data point is measured at 3 minutes, 6 minutes, 9 minutes, etc.).

Example primary data points and probing potential modulations are now described. While described primarily with regard to voltage pulses or voltage steps, it will be understood that other types of probing potential modulations may be used as previously described. With reference to FIG. 7A, 0.55V is applied to the working electrode of an analyte sensor (e.g., a glucose sensor having a chemical composition such as glucose oxidase for oxidizing/converting glucose to a product such as $H_2O_2$) relative to a reference electrode such as Ag/AgCl. Other sensor types and/or electrode materials may be used. Continuous current flow through the working electrode is measured at a fixed sampling frequency of 3 minutes periodically, as the primary data points/current signals. Other sampling frequencies may be used.

After each primary data point is measured, probing potential modulations may be applied to the working electrode to probe sensor/electrode status and/or condition, for example. In the embodiment of FIG. 7B-7F, the below described probing potential modulations are applied after each primary data point is measured. Specifically, in FIGS. 7B-7F, probing potential modulations are employed after the primary data point is measured at 3 minutes (circle 702) and 6 minutes (circle 704). Similar probing potential modulations may be employed after each primary data point is measured (e.g., after 0, 3, 6, 9, 12, 15, 18, etc., minutes). As mentioned, in other embodiments, probing potential modulations may be applied prior to measuring a primary data point (e.g., assuming the primary data point is not measured until probing potential modulation current has decayed away). In some embodiments, probing potential modulations maybe applied prior to and after measuring a primary data point.

With reference to FIG. 7B, six voltage steps (Steps 1-6) may be employed after each primary data point is measured. In the embodiment shown, each step lasts 6 seconds and the resulting working electrode current signal is measured every 2 seconds (resulting in the measurement of 3 current signals per potential step). Other steps in voltage, step durations and/or sampling rates may be used.

Step 1: 0.55V=>0.6V;
Step 2: 0.6V=>0.45V;
Step 3: 0.45V=>0.3V;
Step 4: 0.3V=>0.45V;
Step 5: 0.45V=>0.6V;
Step 6: 0.6V=>0.55V;

Following Step 6, a constant voltage of 0.55V is resumed until the next primary data point is measured and the probing potential modulation sequence is repeated.

With reference to FIG. 7C, six voltage steps (Steps 1-6) may be employed after each primary data point is measured. In the embodiment shown, each step lasts 6 seconds and the resulting working electrode current signal is measured every 2 seconds (resulting in the measurement of 3 current signals per potential step). Other steps in voltage, step durations and/or sampling rates may be used.

Step 1: 0.55V=>0.6V;
Step 2: 0.6V=>0.25V;
Step 3: 0.25V=>0.6V;
Step 4: 0.6V=>0.45V;
Step 5: 0.45V=>0.6V;
Step 6: 0.6V=>0.55V;

Following Step 6, a constant voltage of 0.55V is resumed until the next primary data point is measured and the probing potential modulation sequence is repeated.

With reference to FIG. 7D, four voltage steps (Steps 1-4) may be employed after each primary data point is measured. In the embodiment shown, each step lasts 6 seconds and the resulting working electrode current signal is measured every 2 seconds (resulting in the measurement of 3 current signals per potential step). Other steps in voltage, step durations and/or sampling rates may be used.

Step 1: 0.55V=>0.65V;
Step 2: 0.65V=>0.35V;
Step 3: 0.35V=>0.6V;
Step 4: 0.6V=>0.55V;

Following Step 4, a constant voltage of 0.55V is resumed until the next primary data point is measured and the probing potential modulation sequence is repeated.

With reference to FIG. 7E, six linearly changing voltage steps (Steps 1-6) may be employed after each primary data point is measured. In the embodiment shown, each step lasts 6 seconds and the resulting working electrode current signal is measured every 2 seconds (resulting in the measurement of 3 current signals per potential step). Other steps in voltage, step durations and/or sampling rates may be used.

Step 1: Linear scan from 0.55V=>0.6V, scan rate of 0.00833 V/sec;
Step 2: Linear scan from 0.6V=>0.25V, scan rate of 0.05833 V/sec;
Step 3: Linear scan from 0.25V=>0.6V, scan rate of 0.05833 V/sec;
Step 4: Linear scan from 0.6V=>0.45V, scan rate of 0.025 V/sec;
Step 5: Linear scan from 0.45V=>0.6V, scan rate of 0.025 V/sec;
Step 6: Linear scan from 0.6V=>0.55V, scan rate of 0.00833 V/sec;

Following Step 6, a constant voltage of 0.55V is resumed until the next primary data point is measured and the probing potential modulation sequence is repeated.

For the probing potential modulation examples above, other timing and/or applied voltages may be used. For example, other potential step sequences for different biosensor mediators may be devised.

With reference to FIG. 7F, one potential modulation step is applied to the working electrode, followed by directly returning to the original constant voltage of 0.55V.

Figure 8A:
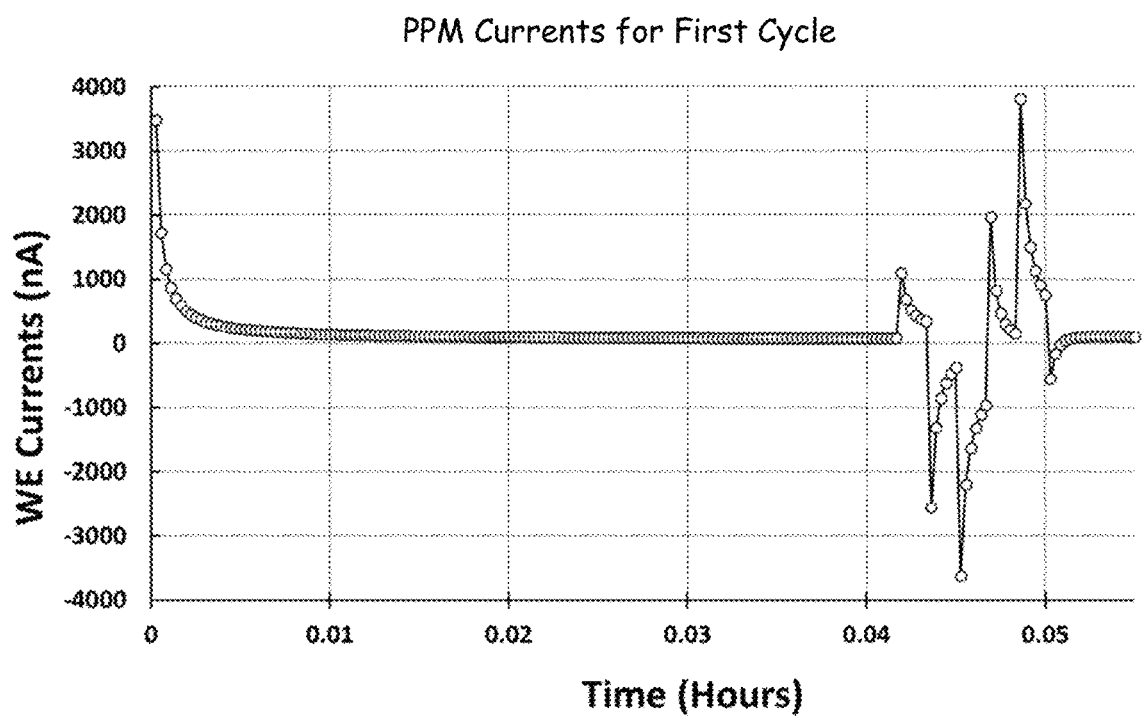
FIG. 8A is an example graph of working electrode (WE) current versus time generated by the probing potential modulations of FIG. 7B during the first cycle of the probing potential modulations in accordance with embodiments provided herein.
Figure 8B:
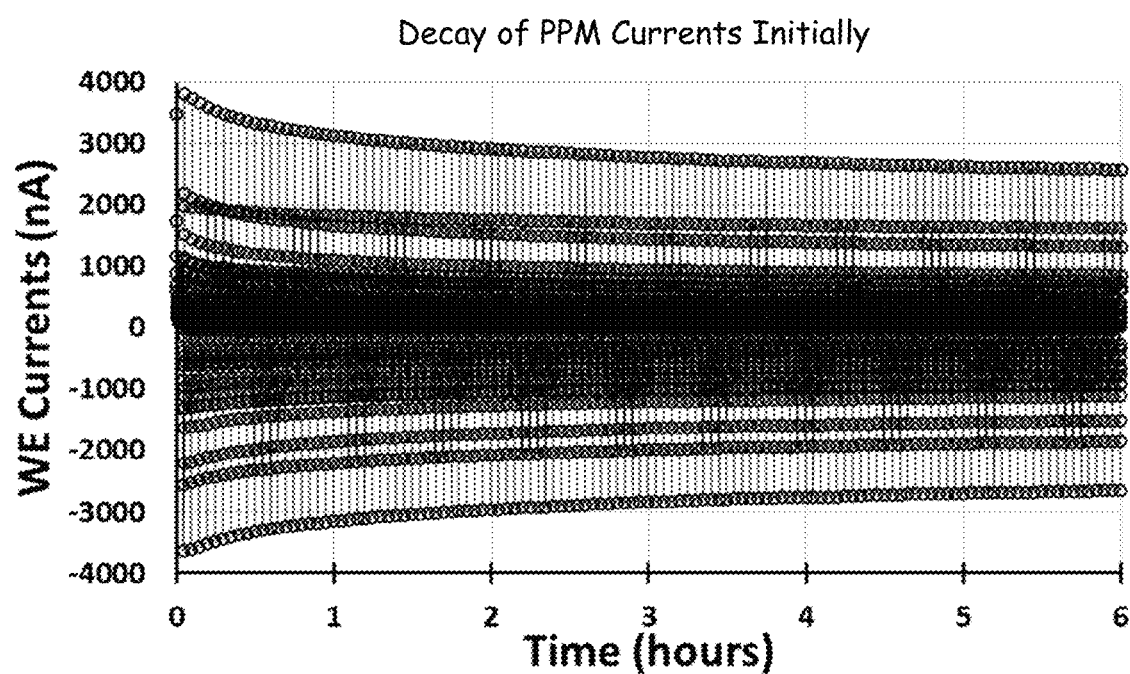
FIG. 8B is a graph of WE current versus time which illustrates decay of the probing potential modulations currents of FIG. 8A in the first 6 hours following probing.

FIG. 8A is an example graph of working electrode (WE) current versus time generated by the probing potential modulations of FIG. 7B during the first cycle of the probing potential modulations in accordance with embodiments provided herein. In this example, a CGM glucose sensor was placed in a 100 mg/dL glucose solution. FIG. 8B is a graph of WE current versus time which illustrates decay of the probing potential modulation currents of FIG. 8A in the first 6 hours. A sample rate of 1-second/point was employed throughout. FIG. 8B provides an overall view of all probing potential modulation (PPM) currents where the outer contour of the profile shows a clear decay behavior, indicating that PPM currents have embedded information about the decay nature of sensor currents after sensor insertion and activation. Because PPM currents have embedded information about sensor current decay, PPM currents may be used as self-sufficient information to correct for the transient nature of sensor sensitivity. Warmup time may then be shortened, as shown below, instead of waiting for a sensor to reach a meta-steady state.

Figure 9A:
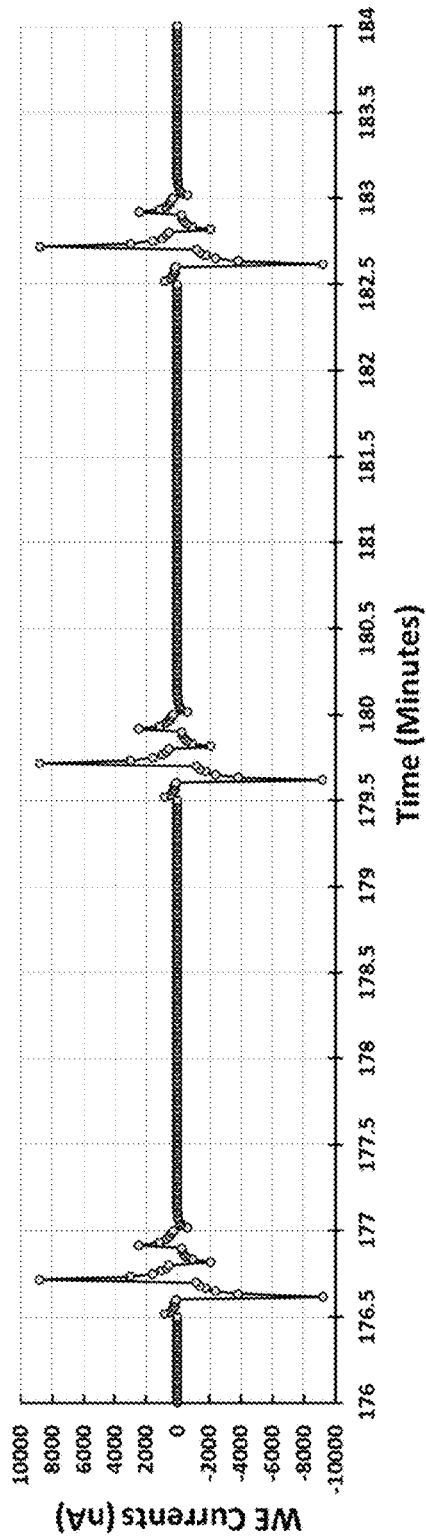
FIG. 9A is an example graph of working electrode (WE) current versus time generated by the probing potential modulations of FIG. 7C in response to three consecutive cycles of probing potential modulations at a constant glucose concentration in accordance with embodiments provided herein.
Figure 9B:
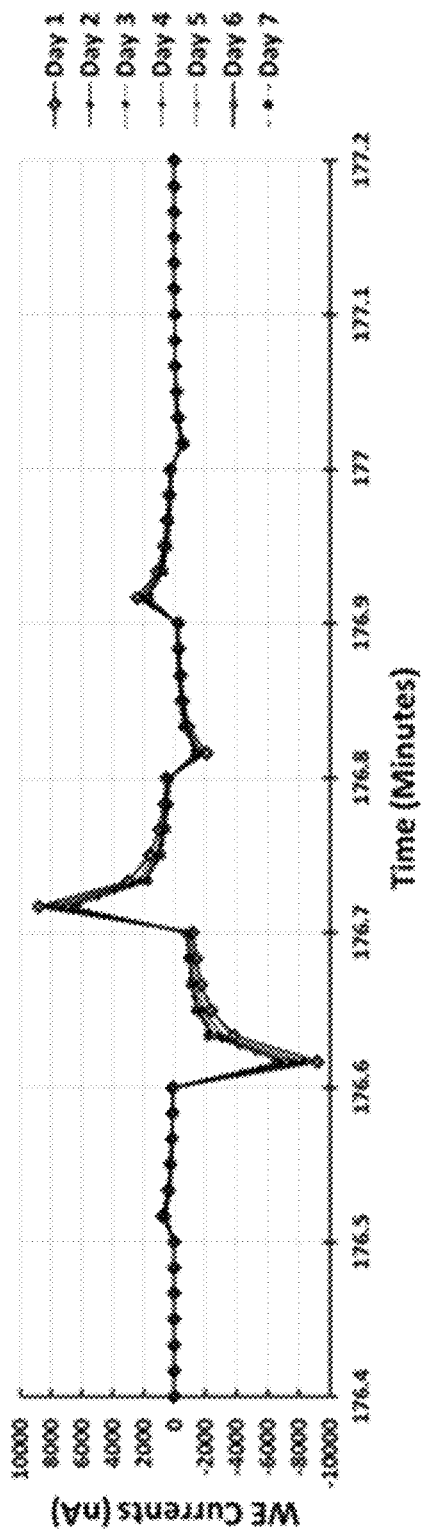
FIG. 9B is a graph of WE current in response to the probing potential modulations of FIG. 7C taken on seven different days (Day 1-Day 7) at a constant glucose concentration.

FIG. 9A is an example graph of working electrode (WE) current versus time generated by the probing potential modulations of FIG. 7C in response to three consecutive cycles of probing potential modulations in accordance with embodiments provided herein. In this example, a CGM glucose sensor was placed in a 100 mg/dL glucose solution. FIG. 9B is a graph of WE current in response to the probing potential modulations of FIG. 7C taken on seven different days (Day 1-Day 7). A sample rate of 1-second/point was employed throughout. A similar WE current response is observed throughout Day 1 and from Day 1 to Day 7.

As shown in the above two examples of FIGS. 8A, 8B, 9A and 9B, in some embodiments, the current signals of the probing region and the non-probing potential modulation region may be measured at a fixed sampling rate such as 1-sec/point. In other embodiments, different sampling rates may be employed. For example, the primary data points may be measured at a slower sample rate of 1, 2, 3, 5, 10 or 15 minutes while the probing potential modulation currents may be measured at a sample rate of 0.5, 1, 2, 3 or 5 seconds within each potential step. The primary data points may be further measured as an average of multiple signals at the constant applied voltage within a close time range of the periodic sample time (e.g., every 3 minutes) such as within 60, 30, 20, 10, or 5 seconds, to reduce the random signal noise. The same may be done for the probing potential modulation currents within 0.1, 0.2 or 0.5 sec of the periodic sample time (e.g., every 1 second), depending on the A-D conversion speed. Other sample rates and/or sampling schemes may be used.

It can be seen from FIGS. 8A, 8B, 9A and 9B that the magnitudes of the probing potential modulation currents (the "ppm" or "PPM" currents) are substantially larger than the otherwise steady-state currents (the non-probing or "nppm" or "NPPM" currents measured without probing potential modulation perturbations). Without wishing to be bound by any theory, the goal of the probing potential modulations is to create perturbated output currents in a short time period to obtain sensor status/condition information while primary data points are measured without the effects of the probing potential modulations. That is, primary data points are measured when the WE current has returned to the otherwise flat current profile generated at the constant voltage $E_0$. It is postulated that there is a wealth of information about the sensor/electrode status/condition embedded in the ppm currents generated by the probing potential modulations. As mentioned, the probing potential modulations may be applied before or after a primary data point is measured. In some embodiments, probing potential modulation output currents may be generated on at least one side of the otherwise flat current profile measured as a primary data point. In other embodiments, probing potential modulation output currents may be generated on both sides of the otherwise flat current profile measured as a primary data point. In yet other embodiments, negative and positive probing potential modulation output currents may be generated on both sides of the otherwise flat current profile measured as a primary data point.

Description of the Probing Potential Modulation Currents

Figure 10:
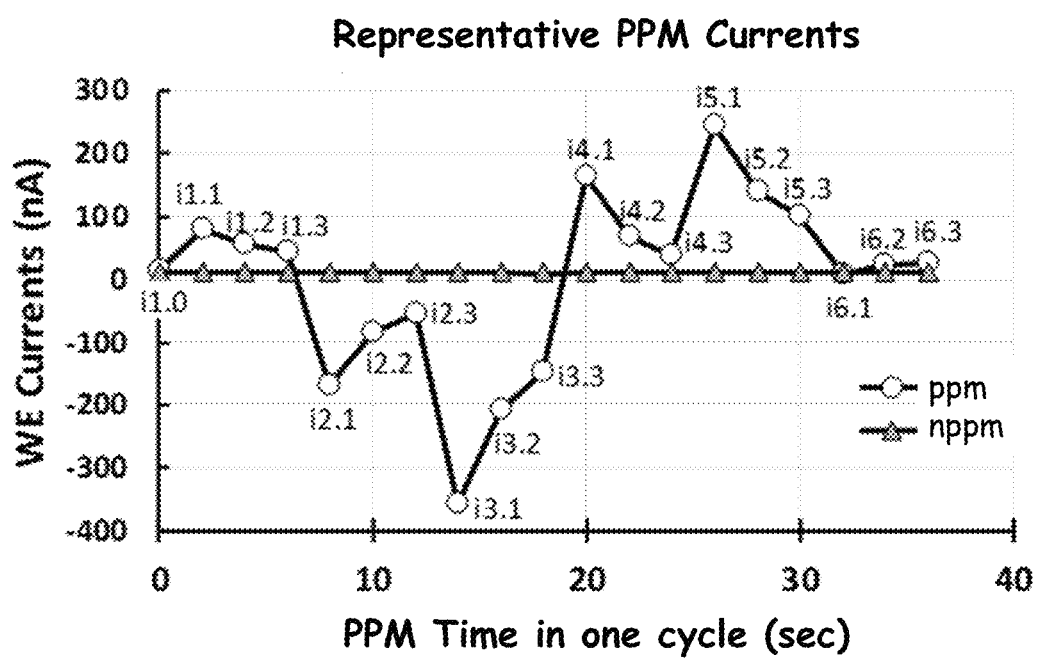
FIG. 10 illustrates a graph of working electrode current versus probing potential modulation time in accordance with an example embodiment.

FIG. 10 illustrates a graph of working electrode current versus probing potential modulation time in accordance with an example embodiment. With reference to FIG. 10, the probing potential modulation steps used to generate the working electrode currents of FIG. 10 are in the following sequence: a forward step from the fixed/constant voltage (e.g., 0.55 volts), followed by two reversed steps, followed by two forward steps, and finalized with a small reversed step to facilitate the returning to the constant potential (e.g., 0.55 Volt), similar to the probing potential modulation steps of FIG. 7B. The probing potential modulation output currents may follow the primary current recorded at the constant potential of 0.55 Volt in one cycle, or the primary data point (as described with reference to FIG. 7B, for example). Probing potential modulation (ppm) output current and non-probing (nppm) output current (e.g., the current due to the constant potential without probing potential modulations) are labelled in FIG. 10. In the embodiment shown, both the ppm current and the nppm current are measured at the same sampling rate of 2-seconds/point (resulting in the measurement of 3 current signals per voltage step, such as i11, i12, i13, i21, i22, i23, etc.). Other sampling rates may be used. In the figures, i10, i11, i12, i13, i21, i22, i23, etc., may be referred to as i1.0, i1.1, i1.2, i2.1, i2.2, i2.3, etc.

Since the probing potential modulations are applied periodically (e.g., after a primary data point is measured) as a potential perturbation to the otherwise constant potential applied to the working electrode, each primary data point may be accompanied by a group of ppm currents. In some embodiments, the period of applying the probing potential modulations may vary from 1 minute up to several hours, and in some embodiments, from about 3-15 minutes when periodic analyte concentration is to be reported. In one particular embodiment, the period of applying probing potential modulations is 3 minutes (e.g., after each primary data point is measured at 3 minute intervals). The minimum time between primary data points may be set based on how soon the output current from the constant potential stabilizes after each probing potential modulation cycle, for example.

As an example, accuracy improvement from use of probing potential modulations is demonstrated by a data set from an in-vitro laboratory study in which CGM sensors were submerged in glucose solutions having four different levels of acetaminophen representing background signals: 0.2 mg/dL, 0.6 mg/dL, 1.2 mg/dL and 1.8 mg/dL. These four levels of acetaminophen are used to simulate different background signals from interference species using acetaminophen as the surrogate molecule for species oxidizable at 0.55 V, as well as the subsequent outcome of correcting the effects of different background signals using PPM currents. The acetaminophen concentration of 0.2 mg/dL is considered to be equivalent to a normal level of interfering background signal while 0.6 mg/dL is considered to be a high level. The 1.2 mg/dL and 1.8 mg/dL acetaminophen concentrations are considered to be extremely high levels. One linearity run at five levels of glucose concentration, 50, 100, 200, 300, 450 mg/dL, was carried out for each level of background acetaminophen.

Figure 11A:
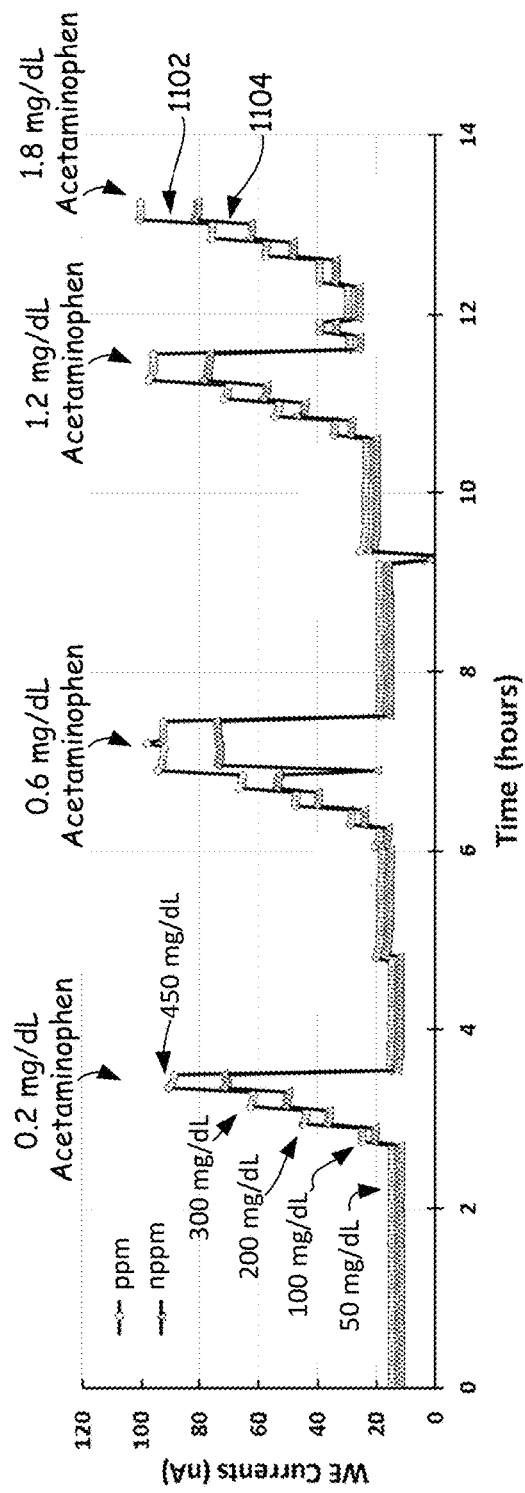
FIG. 11A is a graph of working electrode current versus time that illustrates the temporal response currents of CGM sensors with probing potential modulations (ppm) and with no probing potential modulations (nppm) in response to different glucose concentrations in different acetaminophen concentrations as the background signals in accordance with embodiments provided herein.
Figure 11B:
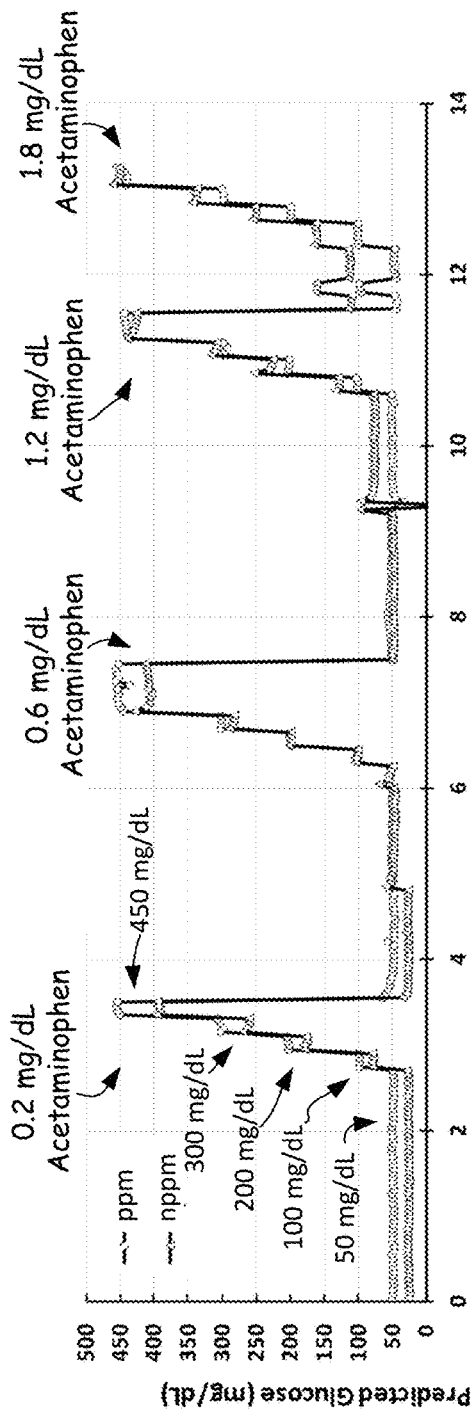
FIG. 11B is a graph of predicted glucose concentration versus time for the WE currents of FIG. 11A based on a simple multi-variate regression.
Figure 11D:
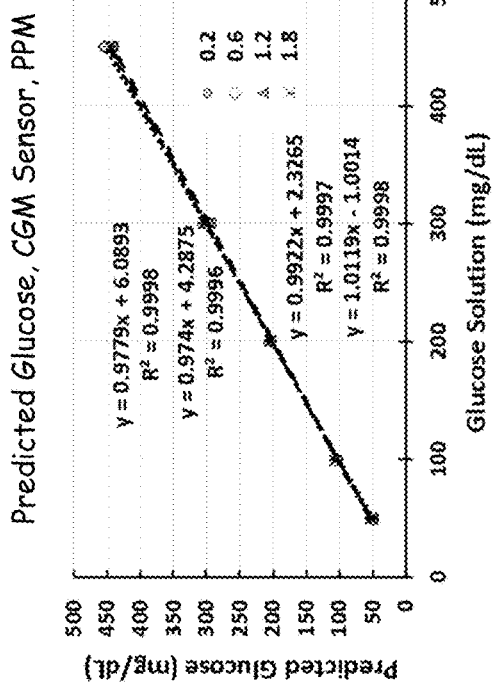
FIG. 11D is a graph of predicted glucose concentration versus glucose solution concentration based on the WE currents of FIG. 11C (which were determined using probing potential modulations).
Figure 11F:
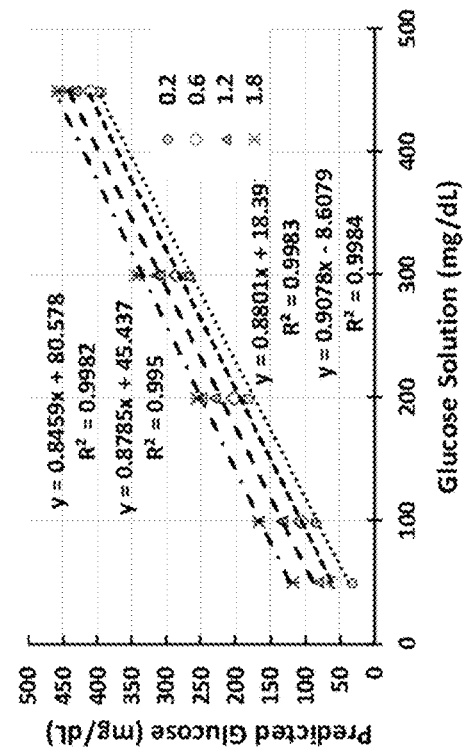
FIG. 11F is a graph of predicted glucose concentration versus glucose solution concentration based on the WE currents of FIG. 11E (which were determined without using probing potential modulations).
Figure 11C:
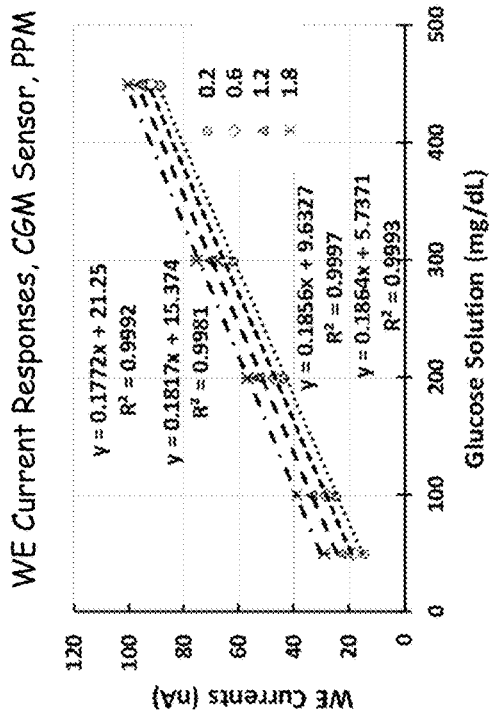
FIG. 11C is a graph of WE current versus glucose solution concentration illustrating response lines for linearity at four levels of acetaminophen with probing potential modulations (ppm) as described herein.
Figure 11E:
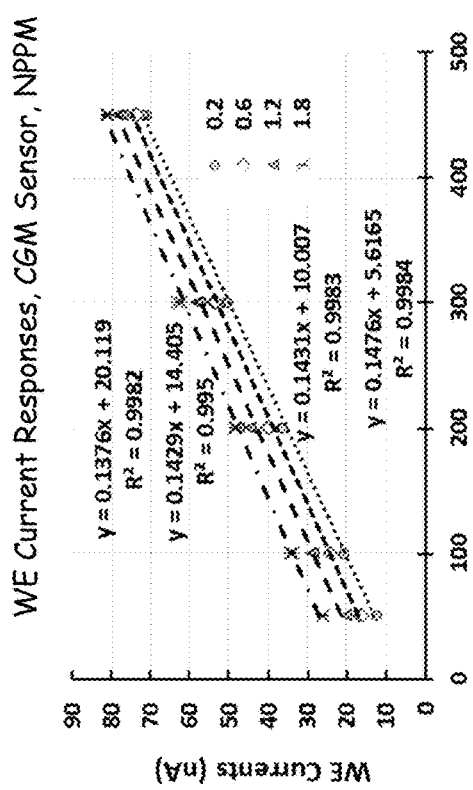
FIG. 11E is a graph of WE current versus glucose solution concentration illustrating response lines for linearity at four levels of acetaminophen without probing potential modulations (nppm).

FIG. 11A is a graph of working electrode currents versus time that illustrates the temporal response currents (the primary data points) of CGM sensors with probing potential modulations (ppm) (curve 1102) and with no probing potential modulations (nppm) (curve 1104) for the above-described samples, in accordance with embodiments provided herein. This graph shows that the current profile of the primary data points with ppm behaves similar to the current profile of the primary data points with no ppm, except that the sensors employed had different sensitivities. This behavior indicates once again that probing potential modulations do not affect the primary data points, but provide additional information about sensors conditions/changes which will be further described below. FIG. 11B is a graph of predicted glucose concentrations versus time for the WE currents of FIG. 11A based on a simple multi-variate regression. FIG. 11C is a graph of WE current versus glucose solution concentration illustrating response lines for linearity at four levels of acetaminophen with probing potential modulations (ppm) as described herein. FIG. 11D is a graph of predicted glucose concentration versus glucose solution concentration based on the WE currents of FIG. 11C (which were determined using probing potential modulations). FIG. 11E is a graph of WE current versus glucose solution concentration illustrating response lines for linearity at four levels of acetaminophen without probing potential modulations (nppm). FIG. 11F is a graph of predicted glucose concentration versus glucose solution concentration based on the WE currents of FIG. 11E (which were determined without using ppm currents). Linear regression equations are shown progressively from lower to upper lines in FIGS. 11C, 11D, 11E and 11F for the four lines corresponding to the four levels of acetaminophen (AA) with increasing intercepts representing the influence from the increasing acetaminophen level.

Table 1 summarizes the response lines (slopes and intercepts) from FIGS. 11C, 11D, 11E and 11F in terms of primary data points and calculated glucose for a sensor employing PPMs and a sensor employing no PPMs. The output glucose values for the probing potential modulation (PPM) and no-PPM methods are calculated from predictive equations (described below) derived from all data of four levels of acetaminophen.

TABLE 1

Summary of effects of added acetaminophen (AA)

| | Levels | AA (mg/dL) | Response Currents | | Response Glucose | |
|---|---|---|---|---|---|---|
| | | | Slope | Intercept | Slope | Intercept |
| PPM | 1 | 0.2 | 0.1864 | 5.7371 | 1.0119 | −1.0014 |
| | 2 | 0.6 | 0.1856 | 9.6327 | 0.9922 | 2.365 |
| | 3 | 1.2 | 0.1817 | 15.374 | 0.974 | 4.2875 |
| | 4 | 1.8 | 0.1772 | 21.25 | 0.9779 | 6.0893 |
| | Average | | 0.1827 | 12.9985 | 0.9890 | 2.9351 |
| No PPM | 1 | 0.2 | 0.1476 | 5.6165 | 0.9078 | −8.6079 |
| | 2 | 0.6 | 0.1431 | 10.007 | 0.8801 | 18.39 |
| | 3 | 1.2 | 0.1429 | 14.405 | 0.8785 | 45.37 |
| | 4 | 1.8 | 0.1376 | 20.119 | 0.8459 | 80.578 |
| | Average | | 0.1428 | 12.5369 | 0.8781 | 33.9325 |

It can be seen from Table 1 that while the average response slopes for the two sensors may be a matter of individual sensor sensitivity from manufacturing, which may vary, the effect of added acetaminophen (AA) as an interferent background substance produces a substantial increase in the intercept. The effect on the intercept is large but similar for the PPM and No PPM data sets. Using the PPM currents as part of the input information to the predictive equation for glucose, the correlation of the output glucose against the reference glucose (represented by the slope, also referred to as "correlation slope") is approaching 1, which is to be expected. If the predictive equation is based on the data from levels 1 and 2, then the maximum effect of the added acetaminophen is within ±6 mg/dL. This level of effect on the output glucose is well within the influence of other factors; that is, the effect is very small compared to the influence from other factors, such as daily sensitivity change. On the other hand, the correlation slope of the output glucose for the No-PPM data is less than 1, reduced by at least 10% due to the overall weighing effect of low and high acetaminophen currents. That is, when a statistical average line is drawn across the four data sets (acetaminophen levels 1, 2, 3 and 4), the correlation slope is affected by the elevated intercept from the level 4 acetaminophen data set. The large effect of the added acetaminophen cannot be removed without additional information such as PPM currents. As such, the maximum effect on the output glucose when no PPM currents are employed is as much as 80 mg/dL in error, which would be 110% for glucose at 70 mg/dL or 80% for glucose at 100 mg/dL.

The primary data point profiles recorded at the 3-minute period are shown in FIG. 11A with five glucose levels in each of four acetaminophen backgrounds. For probing potential modulation (ppm) data from the probing potential modulations, only the primary data points are shown (in the same format as the no-probing potential modulation (nppm) data points). That is, only the responses of the constant operating voltage generated currents to the stimuli of the acetaminophen and glucose are shown for the ppm data in FIG. 11A. The two sensors are shown to have different sensitivities, which is related to the individual sensor sensitivity from manufacturing, instead of being related to the PPM and no-PPM methods. In addition, the effect of the increasing background acetaminophen from the normal level of 0.2 mg/dL to the highest level of 1.8 mg/dL is visible at the low level of glucose at 50 mg/dL. The two data sets of probing potential modulation (ppm) and no-probing potential modulation (nppm) data were analyzed with a simple multi-variate regression using the glucose concentrations as the targets and the primary data point, and in case where ppm data was present, the 18 ppm currents that followed the primary data point (3 per voltage step), as the inputs to the regression to derive a prediction equation for the probing potential modulation data (ppm) and the non-probing potential modulation data (nppm). A statistics software such as Minitab software available from Minitab, LLC of State College, Pa., may be employed for regression analysis, for example.

For the probing potential modulation (ppm) data, the effect of increasing the background acetaminophen is most obvious in the intercepts for the response lines of the four linearity runs with a minor effect on the slopes being observed as shown in FIG. 11C. The predicted glucose plot in FIG. 11D, however, shows the collapse of the four lines virtually into one where the prediction equation incorporates a large number of probing potential modulation (ppm) currents. On the other hand, the effect of different background acetaminophen levels was unable to be overcome by the primary data points only (without probing potential modulation data) where the four separate lines in the glucose signal response plot of FIG. 11E are converted to four separate lines of predicted glucose in FIG. 11F. This comparison shows that the probing potential modulation currents provide rich information to correct for the effect due to background signal variations while the currents from a constant applied voltage are highly susceptible to the background signal variations.

For the no-probing potential modulation (nppm) data, the primary data points alone cannot overcome the substantial changes in the background acetaminophen concentrations, thus giving output glucose values with significant influence from the background interfering species. For the probing potential modulation (ppm) data, there is a group of probing potential modulation (ppm) currents accompanying each primary data point. Review of the glucose prediction equation by regression indicates that 11 out of the 19 inputs (primary data point current from the applied constant potential and 18 probing potential modulation (ppm) currents) are selected as significant in the glucose prediction equation. The probing potential modulation (ppm) currents of significance were from voltage steps 1 through 5. Thus, these probing potential modulation (ppm) currents are self-sufficient information currents which have subtle correlations with different effects for the sensor and/or the working electrode output currents. Subsequently, these probing potential modulation (ppm) currents help formulate a prediction equation for glucose that corrects for different background signals from four levels of acetaminophen.

Example prediction equations based on simple or multivariate regression are provided below. Within these equations, the primary current is labelled as i10. Primary current is the current responsive to the constant voltage potential applied to the working electrode. The primary current is typically measured prior to application of any probing potential modulations, for example. That is, in some embodiments, probing potential modulations are applied to the working electrode after the primary current has been measured. Any number of probing potential modulation steps may be applied (e.g., 1, 2, 3, 4, 5, 6, etc.). Application of a probing potential modulation step causes a non-linear response in working electrode current, which may be measured at multiple times as the response current varies (e.g., 2, 3, 4 or more times) as described previously with reference to FIGS. 7B-7E. Within the prediction equations provided below, probing potential modulation currents are labeled as ixy, where x denotes the voltage step and y denotes at what location (e.g., time) within the voltage step the current is measured. For example, i11 is the first current of the three currents recorded during the first voltage step, while i13 is the third current of the three currents recorded during the first voltage step. Similarly, i63 is the third current of the three currents recorded during the sixth voltage step. As mentioned, i10 is the primary current or current measured at time 0 before probing potential modulations are applied.

For non-probing potential modulation (nppm) data in which only the primary data point currents are used, the nppm prediction equations G_ref_nppm is based on simple regression in equation (3) below. That is, there is only one signal i10 available for expressing the glucose. Even if additional data points were measured in the time period between primary data points (the time when ppm data is measured), because only a constant voltage of 0.55 V is employed, the currents that follow i10 would still contain the same information as i10.

$$G\_ref\_nppm \text{ (mg/dL)} = -43.147657 + 6.14967 * i10 \quad (3)$$

Figure 11G:
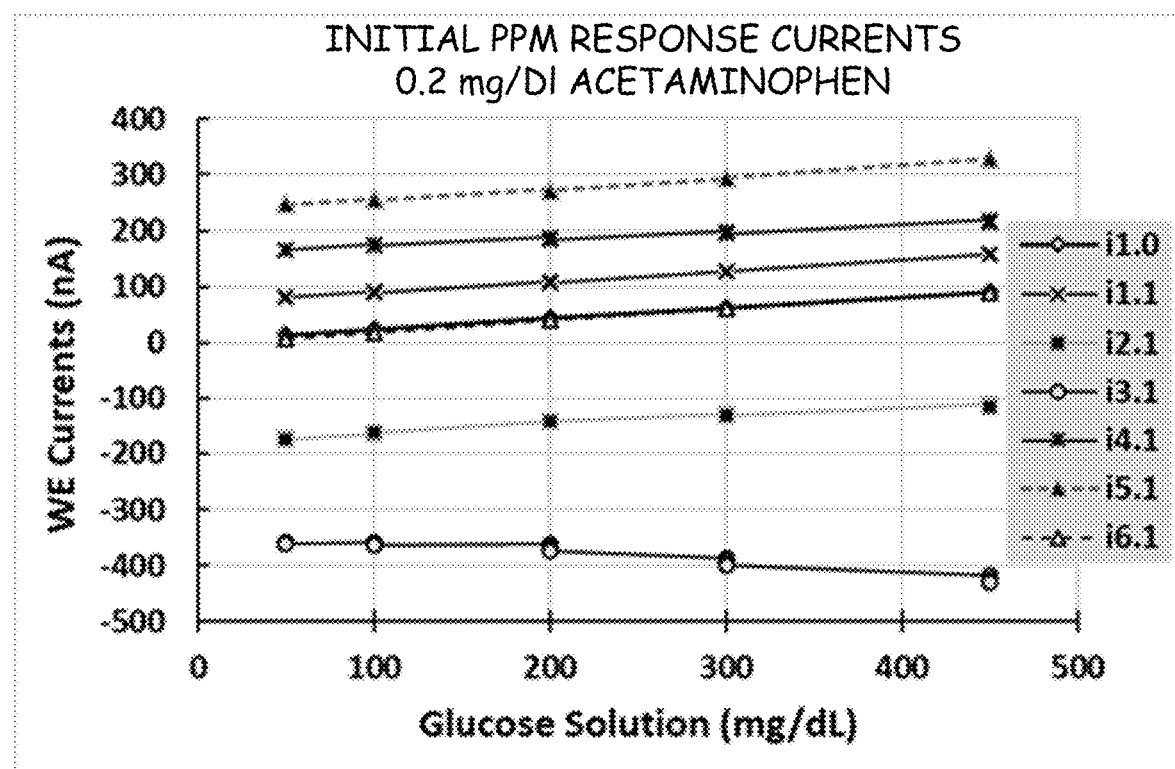
FIGS. 11G and 11H illustrate initial and ending probing potential modulation current correlations, respectively, for an acetaminophen background level of 0.2 mg/dL in accordance with embodiments provided herein.
Figure 11H:
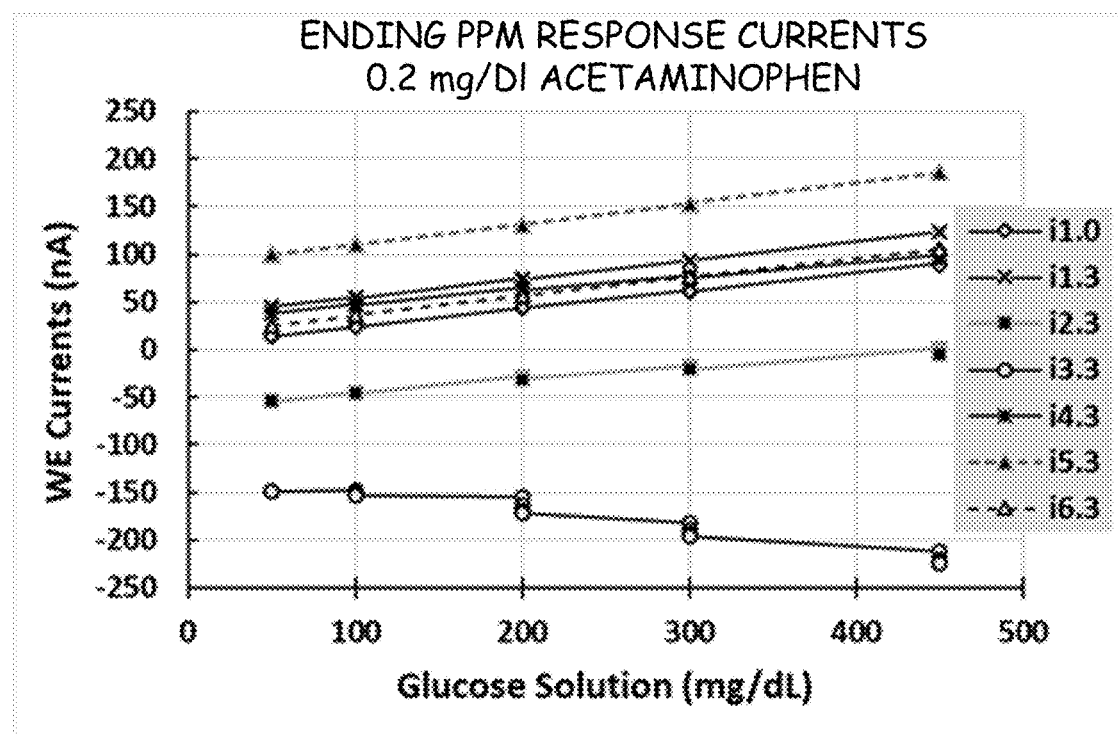

For probing potential modulation (ppm) data in which both primary data point currents and probing potential modulation currents are used, the currents that are generated at different potential modulation steps are different than the generally constant output currents from the constant operating voltage used for measuring primary data points. These ppm currents are correlated with i10 in different ways. As an example of these correlations, two graphs of the initial and ending potential modulation current correlations are shown in FIGS. 11G and 11H for an acetaminophen background level of 0.2 mg/dL, as provided herein. These subtle relationships are built into the prediction equation G_ref_ppm for glucose in equation (4) by multi-variate regression:

$$G\_ref\_ppm \text{ (mg/dL)} = 39.07108 - 11.663917 *$$
$$i11 + 18.212602 * i13 - 9.318668 * i21 + 13.896986 *$$
$$i22 - 9.519628 * i23 - 1.947934 * i31 + 13.389696 *$$
$$i32 - 12.395404 * i33 - 2.851515 * i41 + 9.183032 *$$
$$i42 - 2.944314 * i51 \quad (4)$$

Note that equations (3) and (4) are merely examples. Other prediction equations may be used.

In another example, three CGM sensors were subjected to a long-term (17 day) stability monitoring with probing potential modulations applied every 3-minutes periodically, along with a CGM sensor in the same monitoring employed without the probing potential modulations. Three linearity runs were carried out at time 0 (immediately after the start of the 17-day monitoring), day-7 and day-14. At times other than the linearity runs, the CGM sensors were exposed to a constant glucose solution of 450 mg/dL. The raw current profiles of the primary data points for the four sensors are shown in FIG. 12A, which illustrates a graph of working electrode current versus elapsed time for three sensors subjected to probing potential modulations (sensor ppm-1, ppm-2 and ppm-3) and one sensor subjected to no probing potential modulations (sensor nppm-1). It can be seen that the three sensors employing probing potential modulations (ppm) and the sensor with no probing potential modulations (nppm) track with each other temporarily as working electrode current moves up and down. The relative sensitivities are maintained through the entire monitoring of 17 days. This plot of ppm currents and nppm currents shows that there is no long-term negative effect of probing potential modulation on the primary currents (the currents resulting from the constant operating voltage used to generate primary data points).

There are at least four factors which may contribute to the error in determined glucose concentrations, or affect the accuracy: (1) the initial sensor current decay, or the warmup time which limits the ability of the sensor system to report accurate analyte concentration in early stage; (2) the individual sensor sensitivities among different sensors, or different lots of sensors; (3) the sensitivity changes of the sensors over the monitoring time, and (4) background signal changes due to intakes of interfering substances, such as the medication of acetaminophen.

The three sensors that employed probing potential modulation had different sensitivities with three different sets of calibration constants (slopes and intercepts) in order to determine glucose values accurately if only the primary data information was available. The three sensors sensitivities (slope_1=0.107, Slope_2=0.1532, Slope_3=0.1317) differed by as much as 50% from low to high, which represent significant sensitivity variations. For example, FIG. 12B illustrates working electrode current versus glucose concentration for the three sensors (ppm-1, ppm-2, ppm-3) at day-7 in accordance with embodiments provided herein. The conventional method of factory calibration links the sensitivities at release testing to sensor performance, such as by lot constants, for glucose calculations. If there is any sensitivity change, such as current signals moving up and down, the factory assigned calibration constants (slope and intercept) will lead to error in the determined glucose concentrations.

The initial decay of the sensor currents is a natural tendency of CGM sensors that prevents glucose readings from being reported until a later time, for instance, 1, 2 or 3 or more hours after sensor insertion (see, FIG. 2, for example). This initial quiescent time is referred to the CGM sensor's warmup time. If this warmup time can be reduced, the CGM system may provide glucose readings at a reasonably short time, such as 30 minutes, or even 15, 10, or 5 minutes following insertion.

Sensitivity changes over monitoring time may be seen in FIG. 12C, for example, which illustrates working electrode current versus glucose concentration for one of the sensors (sensor ppm-1) at day-1, day-7 and day-14 in accordance with embodiments provided herein. As shown in FIG. 12C, the sensitivity of the sensor changes (e.g., decreases) over time.

Figure 12D:
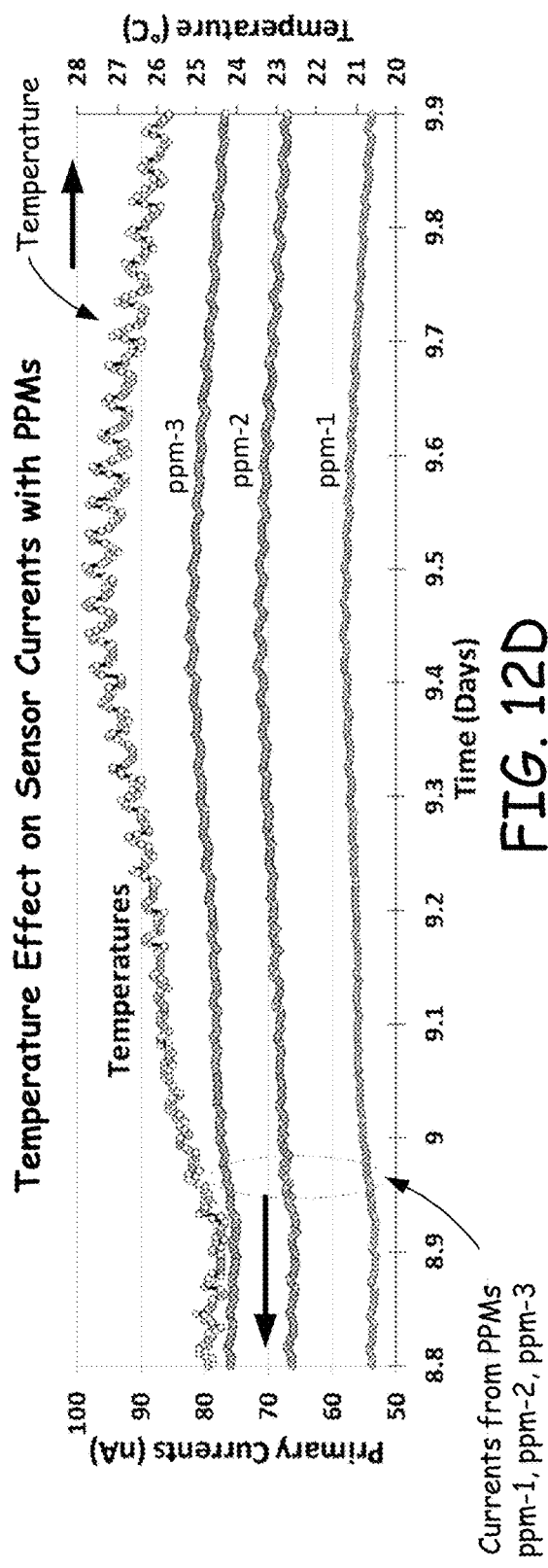
FIG. 12D which illustrates working electrode (primary current) of three sensors with temperature variations during a portion of day-9 of long-term monitoring in accordance with embodiments provided herein.

Sensor current is also dependent on temperature, as shown in FIG. 12D which illustrates working electrode (primary current) of the three sensors with temperature variations during a portion of day-9 of long-term monitoring.

Because probing potential modulation (ppm) currents contain sensor information, the issues of sensitivity differences, initial warmup time and sensitivity changes during monitoring may be overcome to provide more accurately determined analyte concentrations. For example, a predictive glucose equation may be derived with input parameters such as probing potential modulation currents and primary data point currents, using for example, multi-variate regression. (While the example below employs voltage potential steps, it will be understood that other types of probing potential modulations may be similarly employed.) For the provided example of FIG. 12A, the input parameters may be the following types (which are defined below): (1) primary data point current i10 and probing potential modulation currents i11 to i63, (2) temperature cross terms of the primary data point current i10T and probing potential modulation (ppm) currents i11T to i63T, (3) probing potential modulation (ppm) current ratios R1, R2, R3, R4, R5 and R6 within each potential step for the six steps in the probing potential modulation sequence, (4) x-type parameters, (5) y-type parameters, (6) z-type parameters, and/or (7) the cross terms of the additional parameters. These terms are defined as followed:

Probing currents: The probing potential modulation currents i11, i12, i13, . . . , i61, i62, i63, wherein the first digit (x) of the ixy format denotes the potential step while the second digit (y) denotes which current measurement made after application of the potential step (e.g., the first, second or third measurement).

R parameters: These ratios are computed by the ending ppm current being divided by the first ppm current within one potential step. For example, R1=i13/i11, R2=i23/i21, R3=i33/i31, R4=i43/i41, R5=i53/i51, and R6=i63/i61.

X-type parameters: The general format for this type of parameter is given by the ending ppm current of a later potential step being divided by the ending ppm current of an earlier potential step. For example, parameter x61 is determined by i63/i13 where i63 is the ending ppm current of step 6 in the three recorded currents per step while i13 is the ending ppm current of step 1. Additionally, x61=i63/i13, x62=i63/i23, x63=i63/i33, x64=i63/i43, x65=i63/i53, x51=i53/i13, x52=i53/i23, x53=i53/i33, x54=i53/i43, x41=i43/i13, x42=i43/i23, x43=i43/i33, x31=i33/i13, x32=i33/i23, and x21=i23/i13.

Y-type parameters: The general format for this type of parameter is given by the ending ppm current of a later potential step being divided by the first ppm current of an earlier potential step. For example, parameter y61 is determined by i63/i11 where i63 is the ending ppm current of step 6 in the three recorded currents per step while i11 is the first ppm current of step 1. Additionally, y61=i63/i11, y62=i63/i21, y63=i63/i31, y64=i63/i41, y65=i63/i51, y51=i53/i11, y52=i53/i21, y53=i53/i31, y54=i53/i41, y41=i43/i11, y42=i43/i21, y43=i43/i31, y31=i33/i11, y32=i33/i21, and y21=i23/i11, Z-type parameters: The general format for this type of parameter is given by the first ppm current of a later potential step being divided by the ending ppm current of an earlier potential step. For example, parameter z61 is determined by i61/i13 where i61 is the first ppm current of step 6 in the three recorded currents per step while i13 is the ending ppm current of step 1. Additionally, z61=i61/i13, z62=i61/i23, z63=i61/i33, z64=i61/i43, z65=i61/i53, z51=i51/i13, z52=i51/i23, z53=i51/i33, z54=i51/i43, z41=i41/i13, z42=i41/i23, z43=i41/i33, z31=i31/i13, z32=i31/i23, and z21=i21/i13.

Temperature cross terms: Temperature cross terms are computed by multiplying other parameters by the temperature at which the underlying currents were measured. For example, R1T=(i13/i11)*T, y61T=(i63/i11)*T, etc.

Other types of parameters, such as the ppm current differences or relative differences carrying the equivalent or similar information, or the ratios of middle ppm currents, may also be used.

For demonstrating the feasibility of overcoming the issues of different sensor sensitivities, initial warmup time, sensitivity changes over the long-term, and different background signals due to the intake of different amounts of interfering substances, the above parameters, along with their temperature cross terms, are employed as the inputs in multi-variate regression in its simple form. Additional terms/parameters may be provided in the regression analysis.

Equation 5 below shows the regression equation for predicting glucose with the ppm data from the three sensors (ppm-1, ppm-2, ppm-3) in the 17-day long-term monitoring with three linearity runs of FIGS. 12A-D. In addition to the subtle relationships between individual ppm currents shown in FIGS. 11G and 11H, the different ratio parameters defined previously may also be selected and built into the prediction equation. The selected parameters in the resulting equation from this multi-variate regression are the probing currents and the related parameters, also referred to as "self-sufficient information" parameters, which are otherwise not available when only a constant voltage potential is used. The parameters and/or coefficients in Equation 5 are merely examples. Other number and/or types of parameters and/or coefficients may be used.

$$\begin{aligned}G\_ref\ (mg/dL) =& -3428.448 + 27.64708* \\ & i10 - 19.990456*i11 + 5.820128*i13 - 1.933492* \\ & i21 + 5.18382*i31 - 5.131074*i32 - 3.451613* \\ & i33 + 5.493953*i41 + 23.541526*i43 + 0.41852* \\ & i51 - 1.125275*i10T + 0.673867*i11T + 0.196962* \\ & i21T - 0.202042*i31T + 0.271105* \\ & i32T - 0.102746*i41T - 0.047134* \\ & i42T - 0.889602*i43T + 0.06569*i52T - 0.374561* \\ & i63T + 2158.6*R1 + 5210.274*R3 + 3880.969* \\ & x62 + 195.9686*x51 + 2939.115*x53 + 500.49* \\ & x54 + 2519.018*x42 - 2445.111*z53 - 320.966* \\ & z41 + 9593.727*y64 + 4002.55*y53 - 2736.6* \\ & y54 - 11649.06*y41 - 43811.72*y43 + 978* \\ & y31 - 66.3105*R4T + 62.13563*x61T - 170.8194* \\ & x62T + 19.64226*x52T - 75.8533* \\ & x53T - 61.46921*x42T + 10.023384* \\ & z52T + 72.26341*z53T - 5.7766*z54T - 4.099989* \\ & z41T + 16.754378*z32T - 18.354153* \\ & z21T + 309.6468*y61T - 1538.808* \\ & y65T + 83.124865*y51T \end{aligned} \quad (5)$$

Figure 13A:
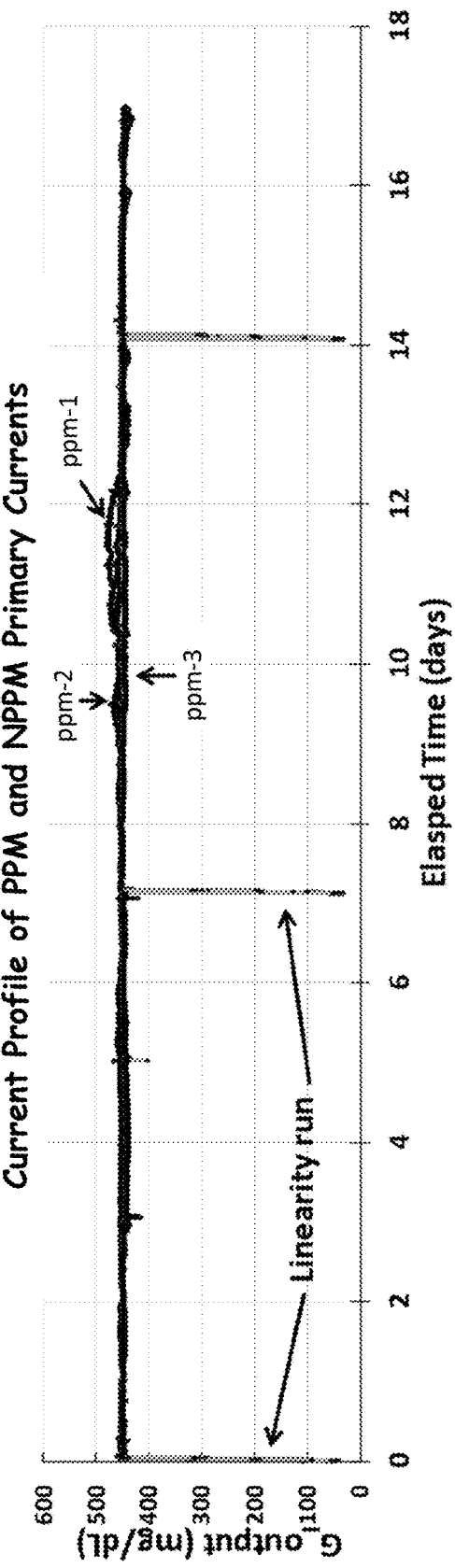
FIG. 13A illustrates output glucose values over 17 days where the differences in glucose values are reduced and the overall glucose accuracy increased through use of probing potential modulations in accordance with embodiments provided herein.
Figure 13B:
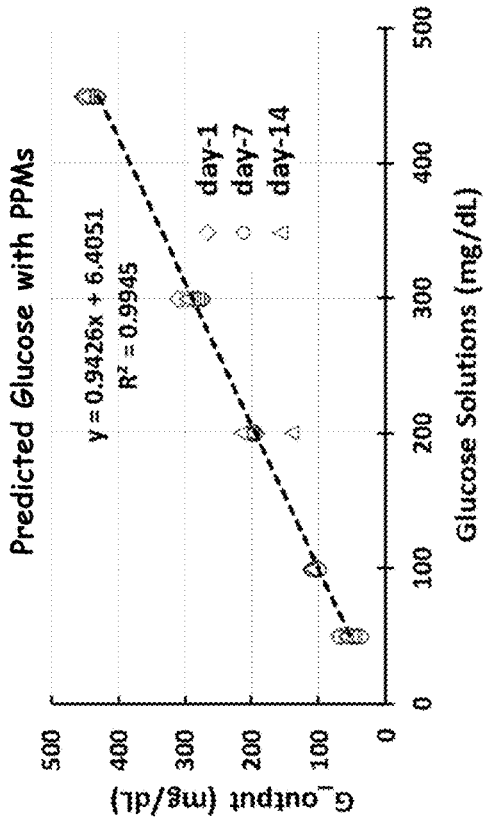
FIG. 13B shows improvement in three glucose response lines for different sensors through use of probing potential modulations in accordance with embodiments provided herein.

The results of the regression after applying Equation 5 to the data of FIGS. 12A-D may be further demonstrated with improved glucose accuracy in FIG. 13A-13F. Corresponding to the current profiles of the three sensors ppm-1, ppm-2 and ppm-3 of FIG. 12A (each having a different sensitivity), FIG. 13A shows the output glucose values over the 17 days where the differences in glucose values are reduced and the overall glucose accuracy increased with probing potential modulation signals feeding the predictive equation for glucose determination (Equation 5). Additionally, the wrinkles in the current profiles due to sensitivity changes and temperature effects over the 17-day monitoring are also smoothed out. Comparing FIGS. 12B and 13B, FIG. 13B shows the three glucose response lines for sensors ppm-1, ppm-2 and ppm-3. The three sensors with widely different sensitivities produce glucose output lines virtually overlapping with each other, which further shows the leveling of the sensitivity differences among the three sensors. If sensors ppm-1, ppm-2 and ppm-3 represent three different release sensor lots from manufacturing, with sensitivities ranging ±25% from the center, then the methods provided herein of using the ppm currents for compensation demonstrate that these methods may accommodate the different sensor sensitivities, and produce high accuracy CGM glucose determinations, without having to relying on factory or in-situ calibration.

Figure 13C:
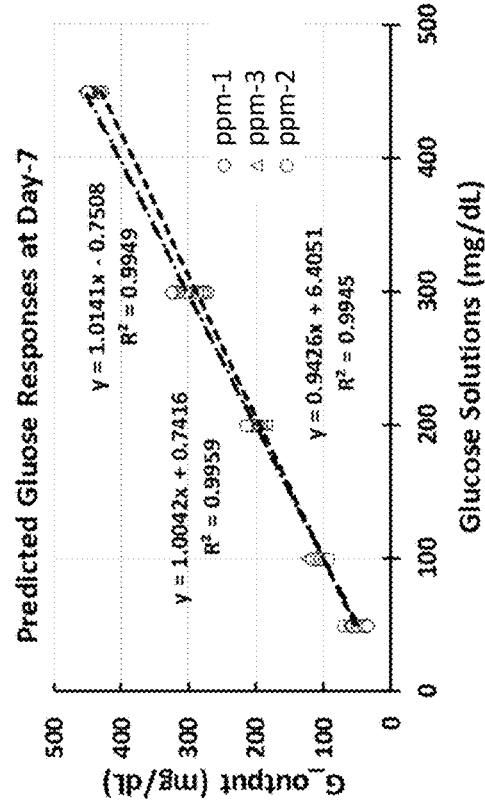
FIG. 13C illustrates the removal of non-linear characteristics during warm up through use of probing potential modulations in accordance with embodiments provided herein.
Figure 13D:
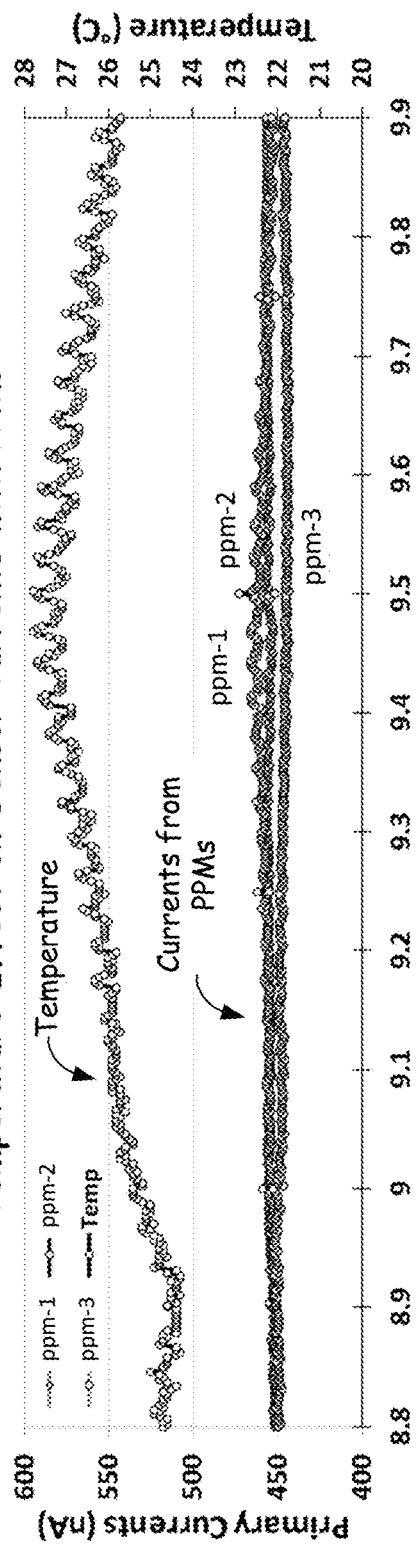
FIG. 13D illustrates reduction of temperature effects through use of probing potential modulations in accordance with embodiments provided herein.
Figure 13E:
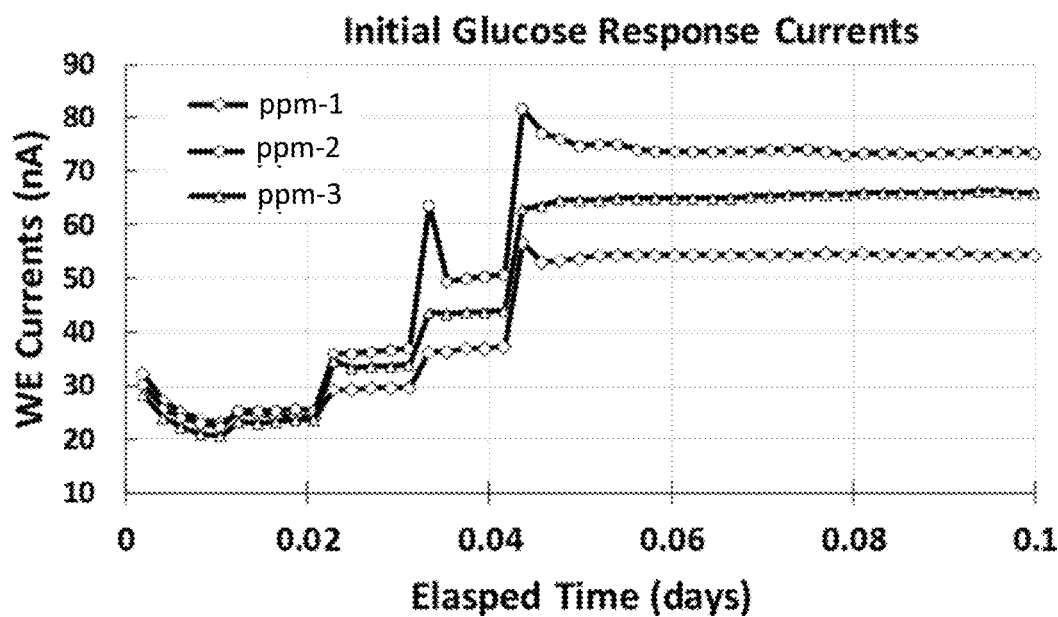
FIGS. 13E and 13F illustrates reduction of sensitivity effects between different sensors through use of probing potential modulations in accordance with embodiments provided herein.
Figure 13F:
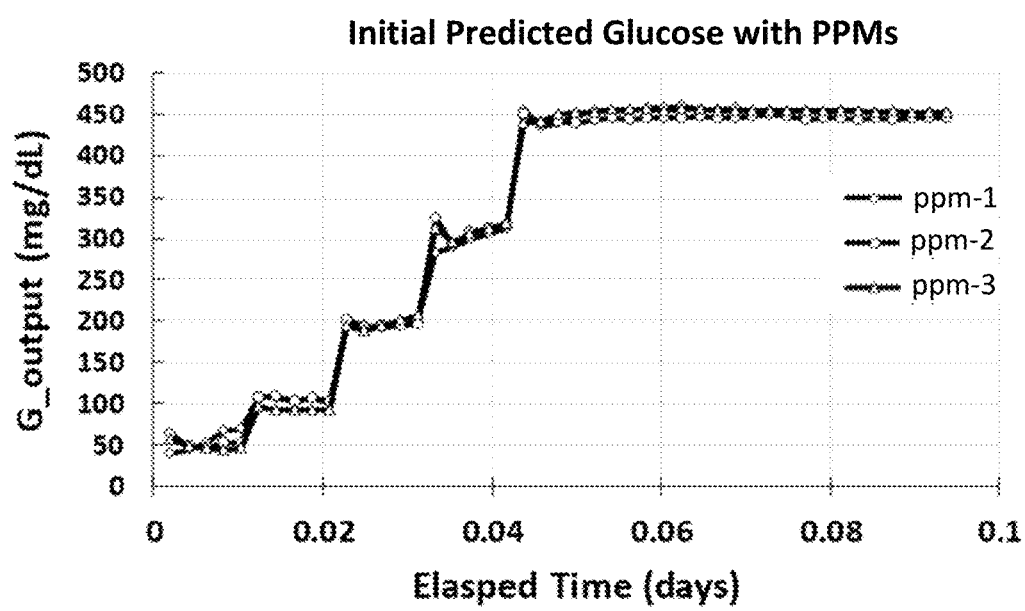

Additionally, comparing FIGS. 12C and 13C, unlike the initial non-linear behavior due to the slow warmup time in the order of 30-40 minutes of FIG. 12C, the output glucose values shown in FIG. 13C at the initial glucose of 50 mg/dL show no non-linear characteristics as these are removed due to the regression, thus making the initial startup time for providing accurate glucose readings as early as 5-10 minutes. The temperature effect shown in FIG. 12D is shown to have been removed in FIG. 13D and with the virtually overlapped glucose profiles from the three sensors ppm-1, ppm-2 and ppm-3. The effect of leveling the sensitivity differences and shortening the warmup time can be further seen in FIG. 13E (raw currents at the beginning of monitoring) and FIG. 13F (the glucose calculated by the prediction equation, Equation 5, with inputs from the ppm currents). A steady-state glucose concentration profile is produced with about 1 hour and the glucose profile of the three sensors align immediately.

In summary, employing probing potential modulations (ppms) as described herein provides enough self-sufficient information to accommodate sensitivity differences among different sensor lots, sensitivity change over an entire continuous monitoring time period, background variations due to different levels of interference species, and non-linear effect of glucose signals immediately after insertion and activation (providing a shortened warmup time). This may be accomplished with ppm currents and without the factory and/or in-situ calibrations.

Figure 14A:
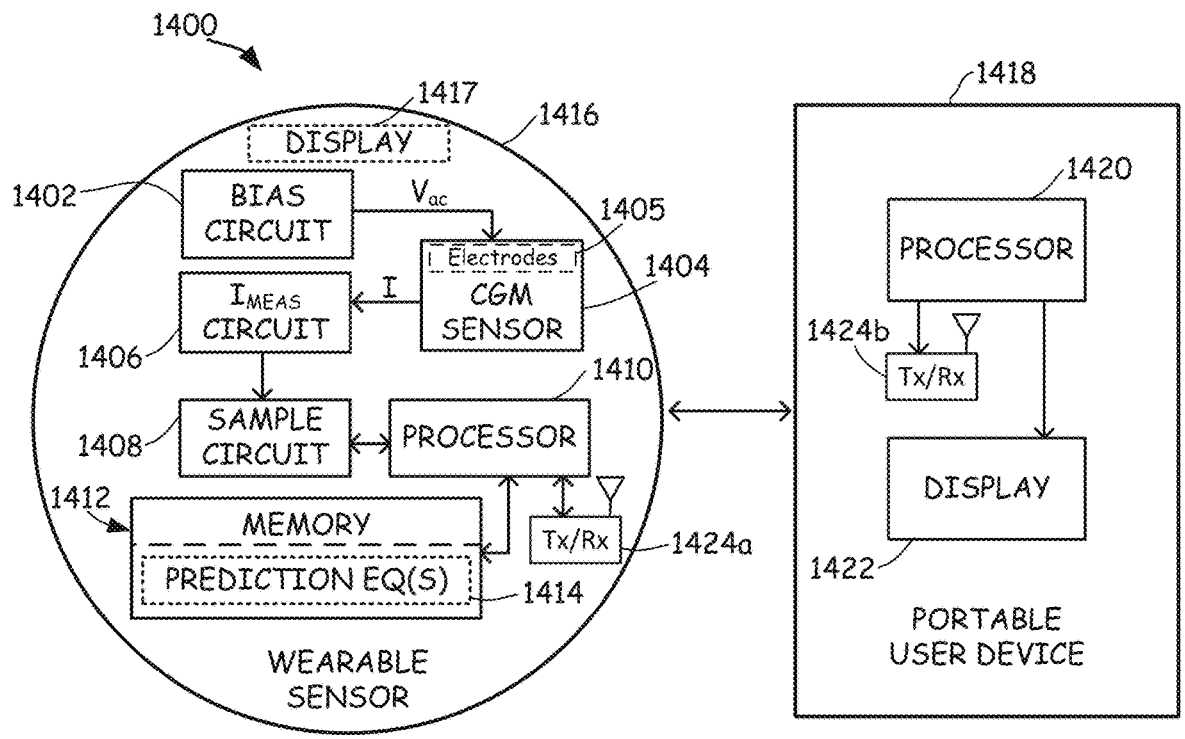
FIG. 14A illustrates a high-level block diagram of an example CGM device in accordance with embodiments provided herein.

FIG. 14A illustrates a high-level block diagram of an example CGM device 1400 in accordance with embodiments provided herein. Although not shown in FIG. 14A, it is to be understood that the various electronic components and/or circuits are configured to couple to a power supply, such as but not limited to a battery. CGM device 1400 includes a bias circuit 1402 that may be configured to couple to a CGM sensor 1404. Bias circuit 1402 may be configured to apply a bias voltage, such as a continuous DC bias, to an analyte-containing fluid through CGM sensor 1404. In this example embodiment, the analyte-containing fluid may be human interstitial fluid, and the bias voltage may be applied to one or more electrodes 1405 of CGM sensor 1404 (e.g., a working electrode, a background electrode, etc.).

Bias circuit 1402 also may be configured to apply a probing potential modulation sequence, as shown in FIGS. 7B-7E or another probing potential modulation sequence, to CGM sensor 1404. For example, probing potential modulation sequences may be applied initially and/or at intermediate time periods as described above with reference to FIGS. 1-6, or applied for each primary data point as described above with reference to FIGS. 7A-13F. Probing potential modulation sequences may be applied before, after, or before and after measurement of a primary data point, for example.

In some embodiments, the CGM sensor 1404 may include two electrodes and the bias voltage and probing potential modulations may be applied across the pair of electrodes. In such cases, current may be measured through the CGM sensor 1404. In other embodiments, the CGM sensor 1404 may include three electrodes such as a working electrode, a counter electrode and a reference electrode. In such cases, the bias voltage and probing potential modulations may be applied between the working electrode and the reference electrode, and current may be measured through the working electrode, for example. The CGM sensor 1404 includes chemicals which react with a glucose-containing solution in a reduction-oxidation reaction, which affects the concentration of charge carriers and the time-dependent impedance of the CGM sensor 1404. Example chemicals include glucose oxidase, glucose dehydrogenase, or the like. In some embodiments, a mediator such as ferricyanide or ferrocene may be employed.

The continuous bias voltage generated and/or applied by bias circuit 1402 may range from about 0.1 to 1 volts versus the reference electrode, for example. Other bias voltages may be used. Example probing potential modulations values are described previously.

Probing potential modulation (ppm) currents and non-probing potential modulation (nppm) currents through CGM sensor 1404 in an analyte-containing fluid responsive to probing potential modulations and a constant bias voltage may be conveyed from CGM sensor 1404 to a current measurement ($I_{meas}$) circuit 1406 (also referred to as current sensing circuitry). Current measurement circuit 1406 may be configured to sense and/or record current measurement signals that have magnitudes indicative of the magnitudes of the currents conveyed from CGM sensor 1404 (e.g., using a suitable current-to-voltage converter (CVC), for example). In some embodiments, current measurement circuit 1406 may include a resistor having a known nominal value and a known nominal precision (e.g., 0.1% to 5%, or even smaller than 0.1%, in some embodiments), through which the current conveyed from CGM sensor 1404 is passed. A voltage developed across the resistor of current measurement circuit 106 represents the magnitude of the current, and may be referred to as the current measurement signal (or raw glucose signal $Signal_{Raw}$).

In some embodiments, a sample circuit 1408 may be coupled to current measurement circuit 1406, and may be configured to sample the current measurement signal, and may produce digitized time-domain sample data that is representative of the current measurement signal (e.g., digitized glucose signals). For example, sample circuit 1408 may be any suitable A/D converter circuit configured to receive the current measurement signal, which is an analog signal, and convert it to a digital signal having a desired number of bits as an output. The number of bits output by sample circuit 1408 may be sixteen in some embodiments, but more or fewer bits may be used in other embodiments. In some embodiments, sample circuit 1408 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio. Any suitable sampling circuitry may be employed.

Still referring to FIG. 14A, a processor 1410 may be coupled to sample circuit 1408, and may be further coupled to a memory 1412. In some embodiments, processor 1410 and sample circuit 1408 are configured to directly communicate with each other via a wired pathway (e.g., via a serial or parallel connection). In other embodiments, the coupling of processor 1410 and sample circuit 1408 may be by way of memory 1412. In this arrangement, sample circuit 1408 writes digital data to memory 1412, and processor 1410 reads the digital data from memory 1412.

Memory 1412 may have stored therein one or more prediction equations 1414 (e.g., Equation 5) for use in determining glucose values based on primary data points (nppm currents) and probing potential modulation (ppm) currents (from current measurement circuit 1406 and/or sample circuit 1408). For example, in some embodiments, two or more prediction equations may be stored in memory 1412, each for use with different segments (time periods) of CGM collected data. In some embodiments, memory 1412 may include a prediction equation based on primary current signals generated by application of a constant voltage potential applied to a reference sensor (e.g., ppm-1, ppm-2 and/or ppm-3 of FIGS. 12A, for example), and a plurality of probing potential modulation current signals generated by application of a probing potential modulation sequence applied between primary current signal measurements.

Additionally or alternatively, memory 1412 may have stored there in calibration indices computed based on potential probing modulation currents for use during in-situ calibrations as described previously.

Memory 1412 also may have stored therein a plurality of instructions. In various embodiments, processor 1410 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 1412 may include instructions that, when executed by the processor 1410, cause the processor 1410 to (a) cause the CGM device 1400 (via bias circuit 1402, CGM sensor 1404, current measurement circuit 1406 and/or sample circuit 1408) to measure current signals (e.g., primary current signals and probing potential modulation current signals) from interstitial fluid; (b) store current signals in memory 1412; (c) compute calibration indices and/or prediction equation parameters such as ratios (and/or other relationships) of currents from different pulses, voltage steps or other voltage changes within a probing potential modulation sequence; (d) employ computed prediction equation parameters to compute glucose values (e.g., concentrations) using prediction equations; (e) compute calibration indices; (e) communicate glucose values to a user; and/or (f) conduct in-situ calibrations based on computed calibration indices.

Memory 1412 may be any suitable type of memory, such as but not limited to, one or more of a volatile memory and/or a non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 112 may be packaged as a single chip or as multiple chips, for example. In some embodiments, memory 112 may be embedded, with one or more other circuits, in an integrated circuit, such as, for example, an application specific integrated circuit (ASIC).

As noted above, memory 1412 may have a plurality of instructions stored therein that, when executed by processor 1410, cause processor 1410 to perform various actions specified by one or more of the stored plurality of instructions. Memory 1412 may further have portions reserved for one or more "scratchpad" storage regions that may be used for read or write operations by processor 1410 responsive to execution of one or more instructions of the plurality of instructions.

In the embodiment of FIG. 14A, bias circuit 1402, CGM sensor 1404, current measurement circuit 1406, sample circuit 1408, processor 1410, and memory 1412 including prediction equation(s) 1414, may be disposed within a wearable sensor portion 1416 of CGM device 1400. In some embodiments, wearable sensor portion 1416 may include a display 1417 for displaying information such as glucose concentration information (e.g., without use of external equipment). Display 1417 may be any suitable type of human-perceivable display, such as but not limited to, a liquid crystal display (LCD), a light-emitting diode (LED) display, or an organic light emitting diode (OLED) display.

Still referring to FIG. 14A, CGM device 1400 may further include a portable user device portion 1418. A processor 1420 and a display 1422 may be disposed within portable user device portion 1418. Display 1422 may be coupled to processor 1420. Processor 1420 may control the text or images shown by display 1422. Wearable sensor portion 1416, and portable user device portion 1418, may be communicatively coupled. In some embodiments the communicative coupling of wearable sensor portion 1416, and portable user device portion 1418, may be by way of wireless communication via transmitter circuitry and/or receiver circuitry, such as transmit/receive circuit TxRx 1424*a* in wearable sensor portion 1416 and transmit/receive circuit TxRx 1424*b* in portable user device 1418, for example. Such wireless communication may be by any suitable means including but not limited to standards-based communications protocols such as the Bluetooth® communications protocol. In various embodiments, wireless communication between wearable sensor portion 1416, and portable user device portion 1418, may alternatively be by way of near-field communication (NFC), radio frequency (RF) communication, infra-red (IR) communication, or optical communication. In some embodiments, wearable sensor portion 1416 and portable user device portion 1418 may be connected by one or more wires.

Display 1422 may be any suitable type of human-perceivable display, such as but not limited to, a liquid crystal display (LCD), a light-emitting diode (LED) display, or an organic light emitting diode (OLED) display.

Figure 14B:
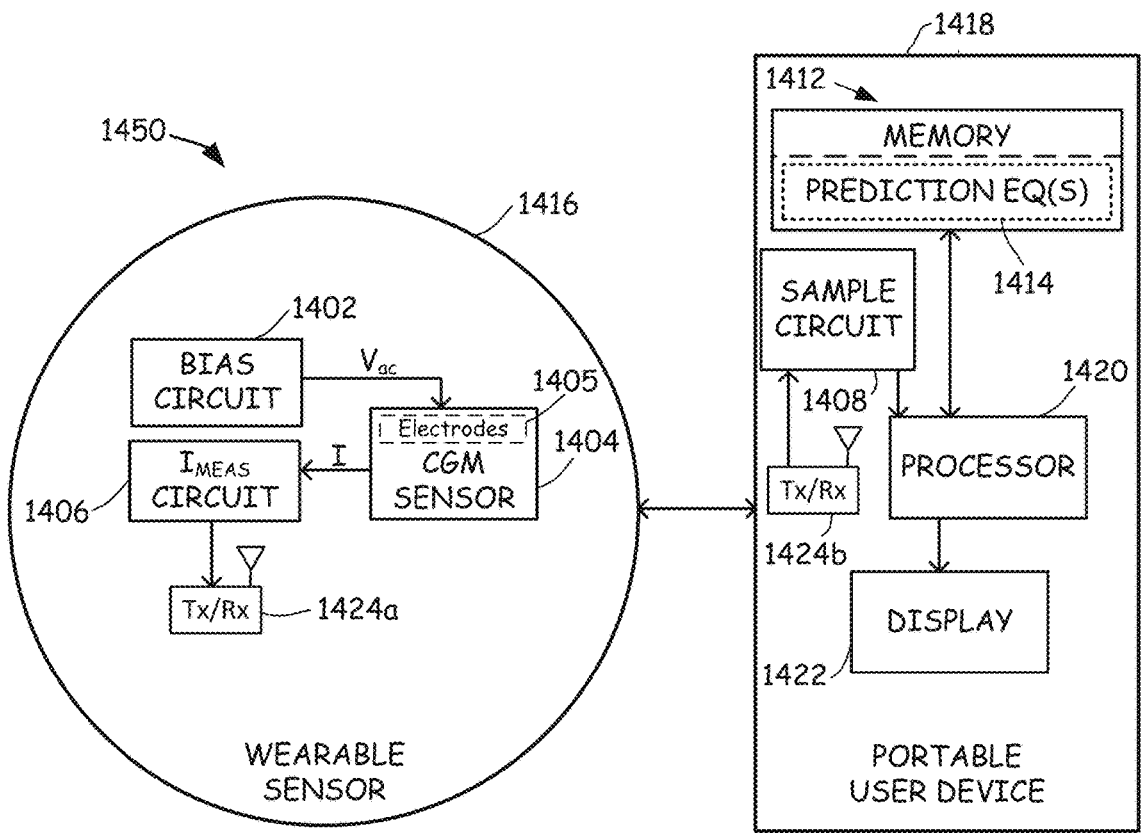
FIG. 14B illustrates a high-level block diagram of another example CGM device in accordance with embodiments provided herein.

Referring now to FIG. 14B, an example CGM device 1450 is shown that is similar to the embodiment illustrated in FIG. 14A, but having a different partitioning of components. In CGM device 1450, the wearable sensor portion 1416 includes the bias circuit 1402 coupled to the CGM sensor 1404, and the current measurement circuit 1406 coupled to the CGM sensor 1404. The portable user device portion 1418 of CGM device 1450 includes the sample circuit 1408 coupled to processor 1420, and the display 1422 coupled to processor 1420. Processor 1420 is further coupled to memory 1412 that may include prediction equation(s) 1414 stored therein. In some embodiments, processor 1420 in CGM device 1450 may also perform the previously-described functions performed by processor 1410 of CGM device 1400 of FIG. 14A, for example. Wearable sensor portion 1416 of CGM device 1450 may be smaller and lighter, and therefore less invasive, than CGM device 1400 of FIG. 14A because sample circuit 1408, processor 1410, memory 1412, etc., are not included therein. Other component configurations may be employed. For example, as a variation to the CGM device 1450 of FIG. 14B, sample circuit 1408 may remain on wearable sensor portion 1416 (such that portable user device 1418 receive digitize glucose signals from wearable sensor portion 1416).

Figure 15:
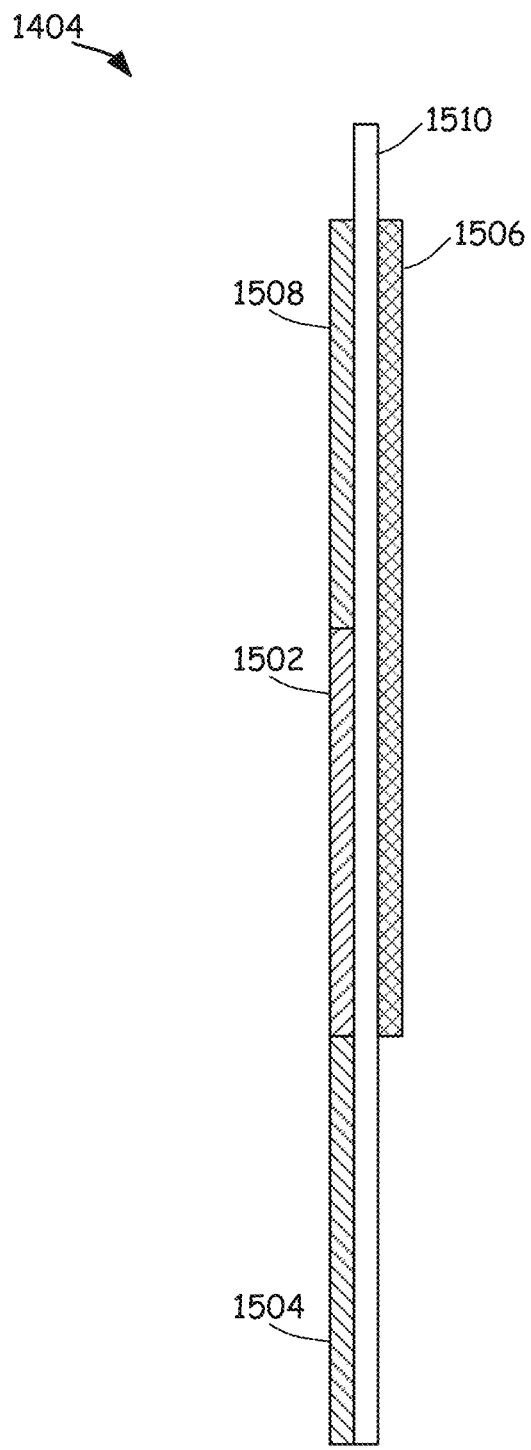
FIG. 15 is a side schematic view of an example glucose sensor in accordance with embodiments provided herein.

FIG. 15 is a side schematic view of an example glucose sensor 1404 in accordance with embodiments provided herein. In some embodiments, glucose sensor 1404 may include a working electrode 1502, a reference electrode 1504, a counter electrode 1506 and a background electrode 1508. The working electrode may include a conductive layer coated with a chemical which reacts with a glucose-containing solution in a reduction-oxidation reaction (which affects the concentration of charge carriers and the time-dependent impedance of the CGM sensor 1404). In some embodiments, the working electrode may be formed from platinum or surface roughened platinum. Other working electrode materials may be used. Example chemical catalysts (e.g., enzymes) for the working electrode 1502 include glucose oxidase, glucose dehydrogenase, or the like. The enzyme component may be immobilized onto the electrode surface by a cross-linking agent such as glutaraldehyde, for example. An outer membrane layer may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, reference electrode 1504 may be formed from Ag/AgCl. The counter electrode 1506 and/or the background electrode 1508 may be formed a suitable conductor such as platinum, gold, palladium, or the like. Other materials may be used for the reference, counter and/or background electrodes. In some embodiments, the background electrode 1508 may be identical to the working electrode 1502, but without the chemical catalyst and mediator. Counter electrode 1506 may be isolated from the other electrodes by an isolation layer 1510 (e.g., polyimide or another suitable material).

While described primarily with regarding to glucose concentration determinations during continuous glucose monitoring, it will be understood that embodiments described herein may be used with other continuous analyte monitoring systems (e.g., cholesterol, lactate, uric acid, alcohol, or other analyte monitoring systems). For example, one or more prediction equations similar to Equation 5 may be developed for any analyte to be monitored through use of probing potential modulation output currents and their related cross terms. Similarly, probing potential modulation output currents may be measured for other analytes and used to compute calibration indices for use during in-situ calibrations.

Figure 16:
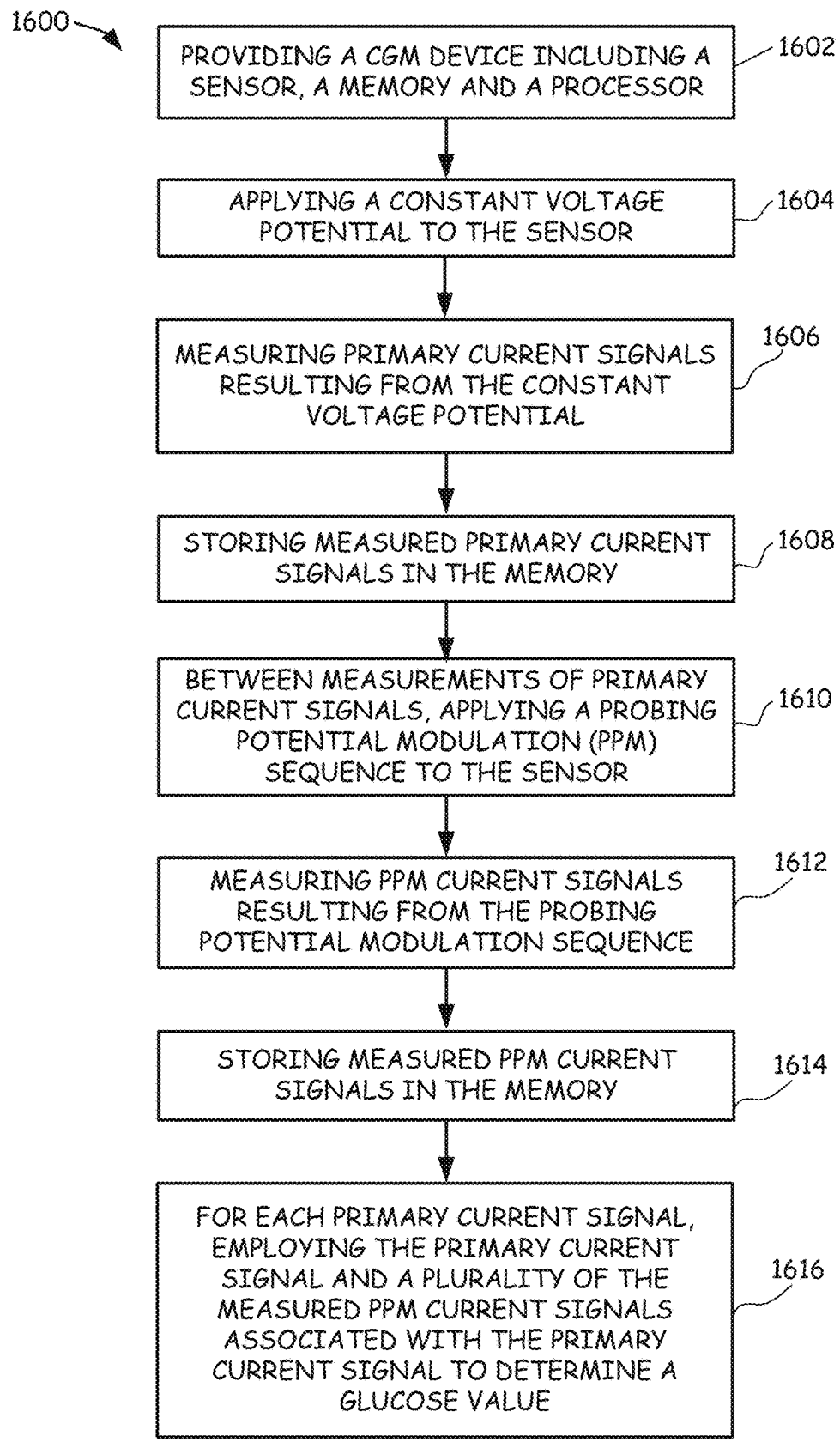
FIG. 16 is a flowchart of an example method of compensating for errors during continuous glucose monitoring (CGM) measurements in accordance with embodiments provided herein.

FIG. 16 is a flowchart of an example method 1600 of compensating for errors during continuous glucose monitoring (CGM) measurements in accordance with embodiments provided herein. Method 1600 includes providing a CGM device including a sensor, a memory and a processor (Block 1602), such as wearable sensor portion 1416 of FIG. 14A, for example. Method 1600 also includes applying a constant voltage potential to the sensor (Block 1604), measuring primary current signals resulting from the constant voltage potential (Block 1606), and storing measured primary current signals in the memory (Block 1608). As described with reference to FIG. 7A, a constant voltage potential may be applied to a working electrode of an analyte sensor. In response to the constant voltage potential, primary current signals may be generated by the sensor, measured and stored in a memory (e.g., memory 412).

Between measurements of primary current signals, method 1600 includes applying a probing potential modulation sequence to the sensor (Block 1610), measuring probing potential modulation current signals resulting from the probing potential modulation sequence (Block 1612) and storing measured probing potential modulation current signals in the memory (Block 1614). For example, FIGS. 7B-7F illustrate example probing potential modulation sequences that may be applied between primary current signal measurements, resulting in probing potential modulation currents that may be measured and stored in memory. For each primary current signal, method 1600 may include employing the primary current signal and a plurality of the measured probing potential modulation current signals associated with the primary current signal to determine a glucose value (Block 1616). In some embodiments, a prediction equation similar to equation 5 may be used to compute glucose values based on primary current signals and probing potential modulation currents measured after (and/or before) each primary current signal, as previously described. The probing potential modulation currents used with a primary current signal to determine a glucose or other analyte value may be referred to as being "associated with" the primary current signal. For example, probing potential modulation currents measured before or after a primary current signal is measured may be associated with the primary current signal (if used to compute a glucose or other analyte value).

Figure 17:
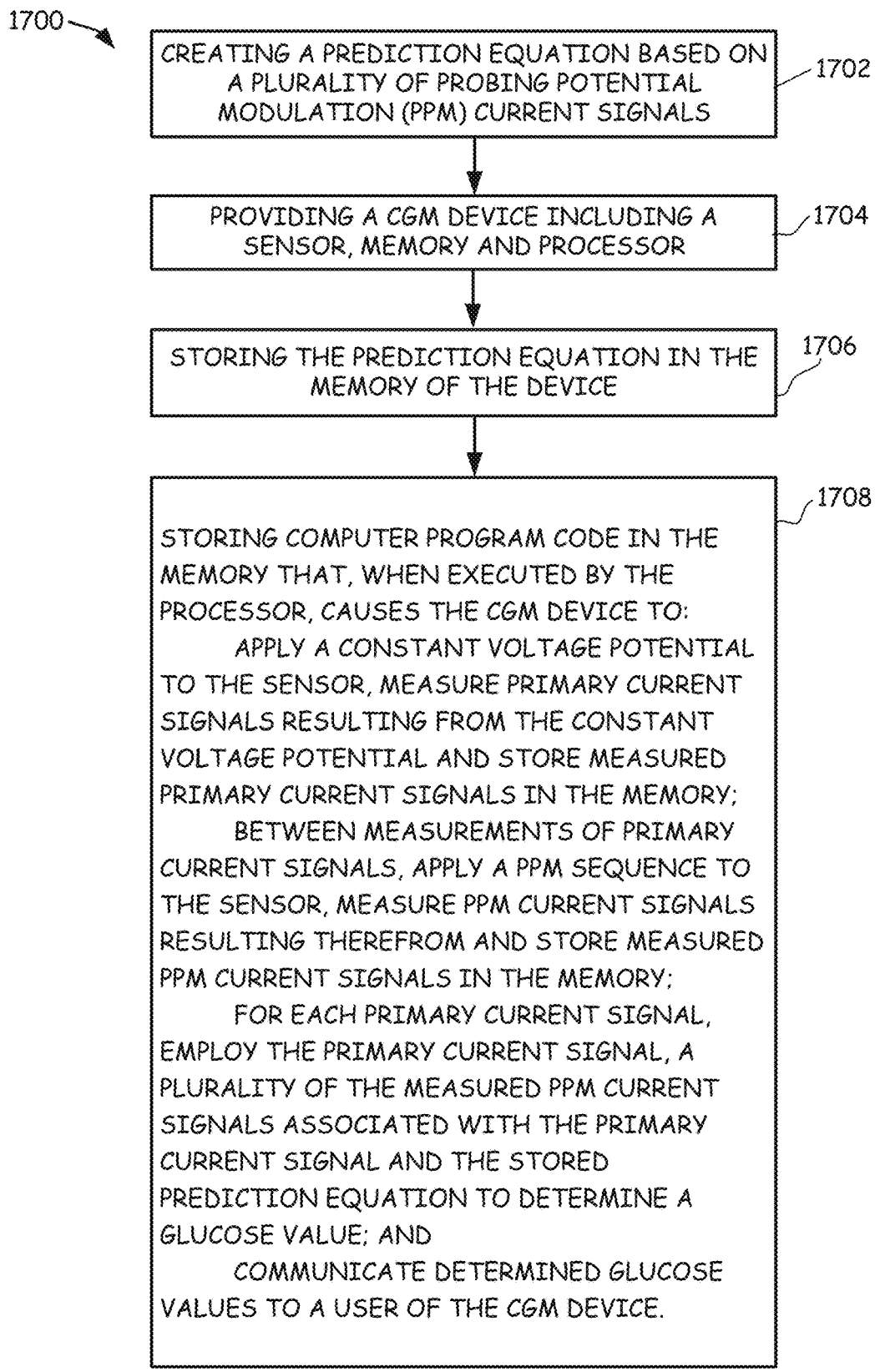
FIG. 17 is a flowchart of an example method of making a continuous glucose monitoring (CGM) device in accordance with embodiments provided herein.

FIG. 17 is a flowchart of an example method 1700 of making a continuous glucose monitoring (CGM) device in accordance with embodiments provided herein. Method 1700 includes creating a prediction equation based on a plurality of probing potential modulation current signals measured for a reference CGM sensor in response to a probing potential modulation sequence applied to the reference CGM sensor before or after primary current signals are measured for the reference CGM sensor (Block 1702). For example, a reference CGM sensor may include one or more CGM sensors used to generate primary data points and ppm currents in response to reference glucose concentrations represented by BGM readings (e.g., primary current and ppm currents measured for the purpose of determining prediction equations that are subsequently stored in a CGM device and used during continuous glucose monitoring).

Method 1700 also includes providing a CGM device including a sensor, a memory and a processor (Block 1704); storing the prediction equation in the memory of the CGM device (1706); and storing computer program code (Block 1708) in the memory of the CGM device that, when executed by the processor, causes the CGM device to (a) apply a constant voltage potential to the sensor, measure primary current signals resulting from the constant voltage potential and store measured primary current signals in the memory; (b) between measurements of primary current signals, apply a probing potential modulation sequence to the sensor, measure probing potential modulation current signals resulting from the probing potential modulation sequence and store measured probing potential modulation current signals in the memory; (c) for each primary current signal, employ the primary current signal, a plurality of the measured probing potential modulation current signals associated with the primary current signal and the stored prediction equation to determine a glucose value; and (d) communicate determined glucose values to a user of the CGM device.

Figure 18:
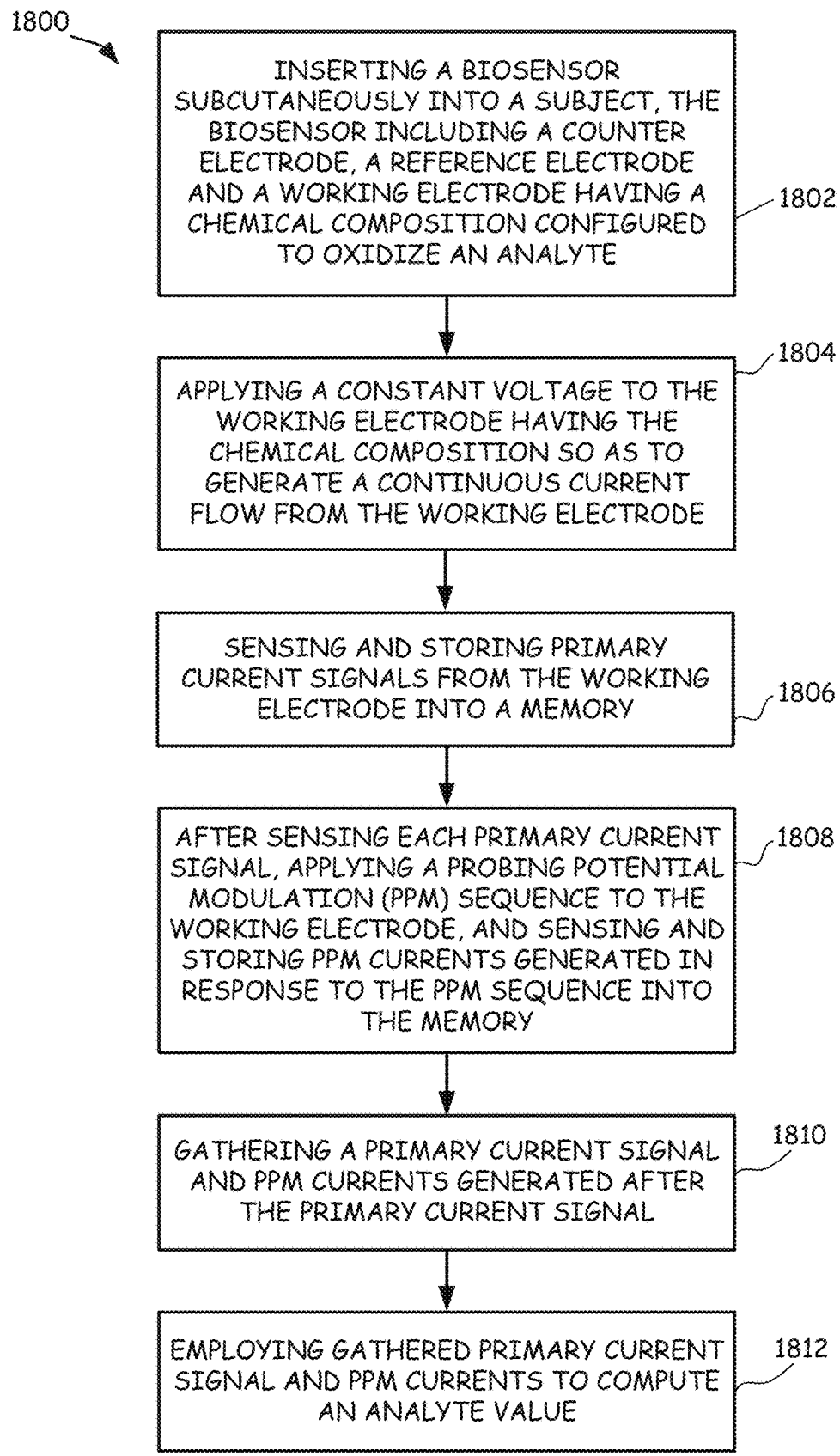
FIG. 18 is a flowchart of an example method of determining analyte concentrations during continuous monitoring measurements in accordance with embodiments provided herein.

FIG. 18 is a flowchart of an example method 1800 of determining analyte concentrations during continuous monitoring measurements in accordance with embodiments provided herein. Method 1800 includes inserting a biosensor subcutaneously into a subject, the biosensor including a counter electrode, a reference electrode and a working electrode having a chemical composition configured to oxidize an analyte (Block 1802); applying a constant voltage to the working electrode having the chemical composition so as to generate a continuous current flow from the working electrode (1804); sensing and storing primary current signals from the working electrode into a memory (1806); after sensing each primary current signal, applying a probing potential modulation sequence to the working electrode, and sensing and storing probing potential modulation currents generated in response to the probing potential modulation sequence into the memory (1808); gathering a primary current signal and probing potential modulation currents generated after the primary current signal (1810); and employing the gathered primary current signal and probing potential modulation currents to compute an analyte value (1812).

Figure 19:
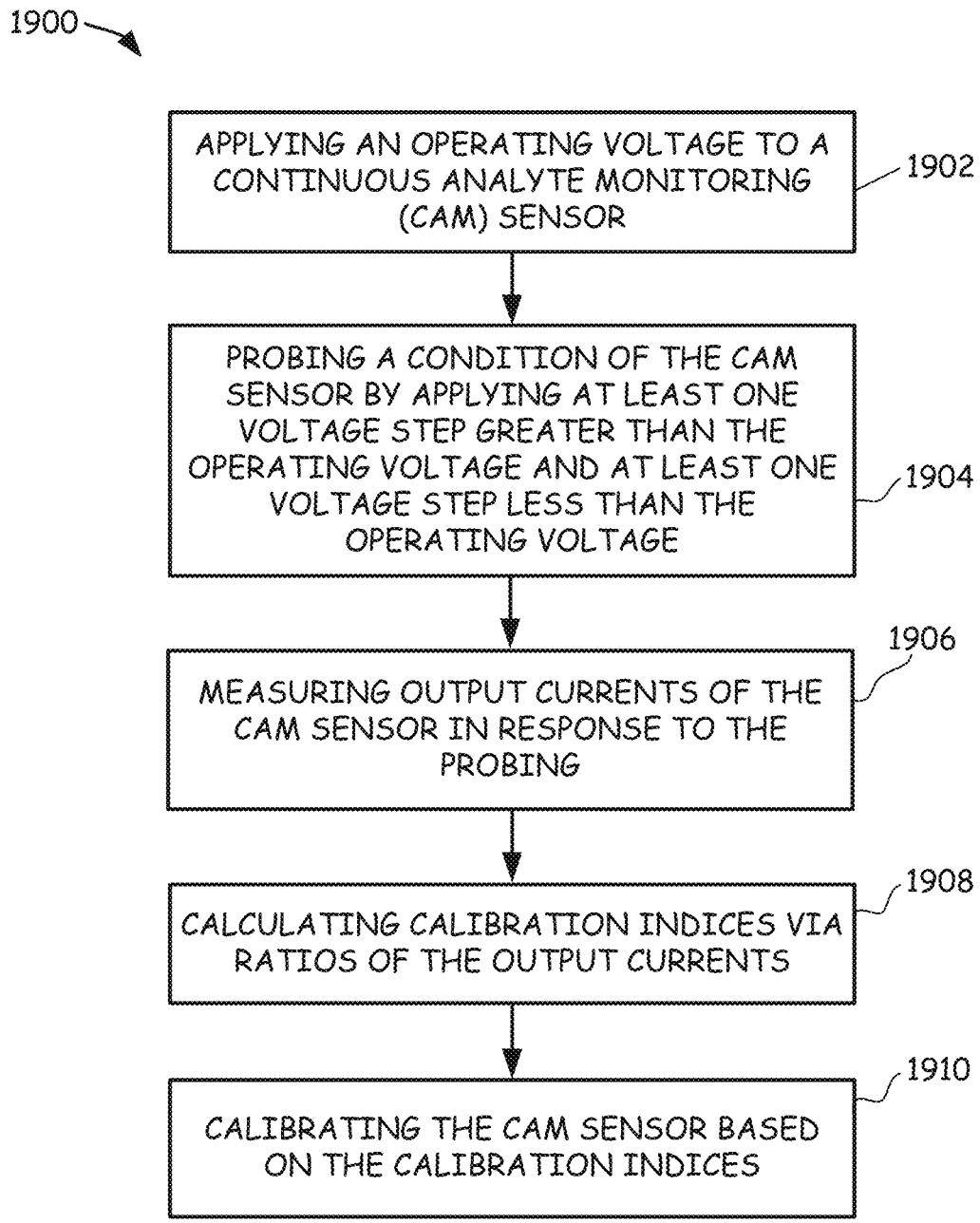
FIG. 19 is a flowchart of an example method of probing a condition of a continuous analyte monitoring (CAM) sensor and of calibrating the sensor based thereon in accordance with embodiments provided herein.

FIG. 19 is a flowchart of an example method 1900 of probing a condition of a continuous analyte monitoring (CAM) sensor and of calibrating the sensor based thereon in accordance with embodiments provided herein. Method 1900 includes applying an operating voltage to the CAM sensor (Block 1902); probing a condition of the CAM sensor by applying at least one voltage potential step greater than the operating voltage and at least one voltage potential step less than the operating voltage (Block 1904); measuring output currents of the CAM sensor in response to the probing (Block 1906); calculating calibration indices via ratios of the output currents (Block 1908); and calibrating the CAM sensor based on the calibration indices (Block 1910).

Figure 20:
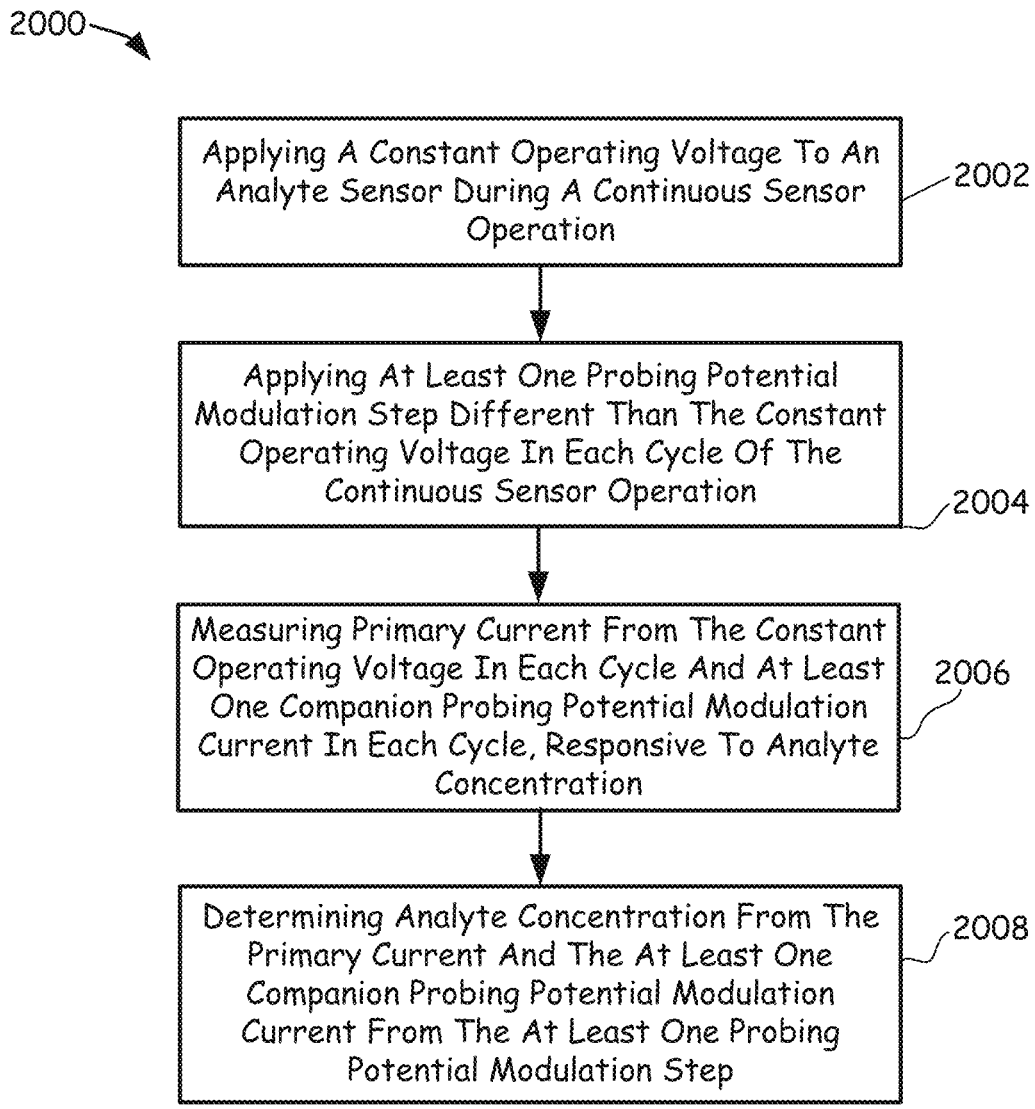
FIG. 20 is a flowchart of an example method of determining an analyte concentration from a continuous analyte monitoring (CAM) sensor and of calibrating the sensor based thereon in accordance with embodiments provided herein.

FIG. 20 is a flowchart of an example method 2000 of applying probing potential modulation during continuous analyte monitoring for determination of analyte concentration in accordance with embodiments provided herein. Method 2000 includes applying a constant operating voltage to an analyte sensor during a continuous sensor operation (Block 2002). For example, a constant voltage potential, such as 0.55 Volts or another suitable value, may be applied to the working electrode of a sensor. Block 2004 includes applying at least one probing potential modulation step different than the constant operating voltage in each cycle of the continuous sensor operation. As shown in FIGS. 7B-7F, a probing potential modulation sequence of voltage steps may be applied to the working electrode of a sensor so as to generate probing potential modulations currents, for example. Block 2006 includes measuring primary current from the constant operating voltage in each cycle and at least one companion probing potential modulation current in each cycle, responsive to analyte concentration. For example, following each measurement of a primary data point (e.g., a current signal caused by the constant operating voltage), probing potential modulation currents may be generated by application of a probing potential modulation sequence and these probing potential modulation currents may be measured (as "companion" probing potential modulation currents to the primary data point). Block 2008 includes determining analyte concentration from the primary current and the at least one companion probing potential modulation current from the at least one probing potential modulation step.

In some embodiments, determining analyte concentration may include accommodating a sensor sensitivity variation of at least ±25% from a center sensitivity of a manufacturing release without factory calibration. That is, large sensitivity variations between sensors may be accommodated through the use of ppm currents, without the use of factory calibrations. Further, in some embodiments, determining analyte concentration may include accommodating effects of background signal changes by at least 5 times. For example, analyte concentrations may be accurately determined by using ppm currents despite a 5 times change in background interference signals as described previously with reference to FIGS. 11A-11F.

In some embodiments, determining analyte concentration may include accommodating daily sensitivity changes without an in-situ calibration. For example, analyte concentrations may be accurately determined by using ppm currents despite daily sensitivity changes as described with reference to FIGS. 13A-13D (without using in-situ calibrations). Likewise, in some embodiments, determining analyte concentration may include determining analyte concentration with a warmup time not longer than 30 minutes as previously described (see, for example, FIG. 12C).

As mentioned, while described primarily with regarding to glucose concentration determinations during continuous glucose monitoring, it will be understood that embodiments described herein may be used with other continuous analyte monitoring systems (e.g., cholesterol, lactate, uric acid, alcohol, or other analyte monitoring systems). For example, in some embodiments, a continuous analyte monitoring (CAM) device may be provided that includes a wearable portion having a sensor configured to be subcutaneously inserted into a subject and to produce current signals from interstitial fluid (e.g., wearable sensor portion 1416), a processor (e.g., processor 1410) and a memory (e.g., memory 412) coupled to the processor. The memory may include computer program code stored therein that, when executed by the processor, causes the CAM device to: (a) apply a constant voltage to the sensor so as to generate a primary current flow from the sensor; (b) sense and store primary current signals generated in response to the constant voltage into the memory; (c) between sensing primary current signals, apply a probing potential modulation sequence to the sensor, and sense and store probing potential modulation currents generated in response to the probing potential modulation sequence into the memory; and (d) employ primary current signals and probing potential modulation currents to compute analyte values over a time period of at least a week (e.g., 7-14 days). In some embodiments, through use of probing potential modulation currents, the CAM device need not employ an in-situ calibration at any point during continuous analyte monitoring (e.g., no finger sticks or in-situ calibration for 7 to 14 days), such as to accommodate for sensor sensitivity changes or background signal changes due to different levels of interference substances. In some embodiments, through use of probing potential modulation currents, the CAM device may have a warm up time of not more than 30 minutes, and in some cases 5-15 minutes or less. Likewise, in some embodiments, use of probing potential modulation currents may eliminate the need for the CAM device to be factory calibrated (e.g., to accommodate lot-to-lot variations).

The foregoing description discloses example embodiments of the disclosure. Modifications of the above-disclosed apparatus and methods which fall within the scope of the disclosure should be readily apparent to those of ordinary skill in the art. Accordingly, while the present disclosure has been disclosed in connection with example embodiments, it should be understood that other embodiments may fall within the scope of the disclosure, as defined by the following claims.

The invention claimed is:

1. A method of continuous analyte monitoring, the method comprising:
applying a constant voltage potential to a sensor of a continuous analyte monitoring device;
determining a primary current signal resulting from the constant voltage potential;
applying a probing potential modulation sequence to the sensor, the probing potential modulation sequence comprising a plurality of voltage steps, the plurality of voltage steps each comprising a change in voltage from the constant voltage potential;
determining a plurality of probing potential modulation current signals resulting from the probing potential modulation sequence;
determining a prediction equation based at least on probing potential modulation current signals determined during at least two voltage steps of the plurality of voltage steps;
determining an analyte value based at least in part on the primary current signal, the plurality of probing potential modulation current signals, and the prediction equation; and
transmitting the analyte value to a user interface of the continuous analyte monitoring device.

2. The method of claim 1, wherein the sensor comprises a working electrode, and wherein the primary current signal and the plurality of probing potential modulation current signals respectively comprise a signal from the working electrode.

3. The method of claim 1, comprising:
determining the primary current signal for a plurality of intervals, the plurality of intervals having a time period of from 3 to 15 minutes; and
determining the plurality of probing potential modulation current signals for respective ones of the plurality of intervals.

4. The method of claim 3, comprising:
for at least some of the plurality of intervals, determining the plurality of probing potential modulation current signals prior to determining the primary current signal.

5. The method of claim 3, comprising:
for at least some of the plurality of intervals, determining the plurality of probing potential modulation current signals immediately after the primary current signal.

6. The method of claim 1, wherein at least some of the plurality of voltage steps differ from one another in respect of one or both of magnitude or duration.

7. The method of claim 1, wherein the plurality of voltage steps comprises at least one increase in voltage above the constant voltage potential and at least one decrease in voltage below the constant voltage potential.

8. The method of claim 1, comprising:
determining a ratio of a first one of the plurality of probing potential modulation current signals to a second one of the plurality of probing potential modulation current signals; and
determining the analyte value based at least in part on the ratio.

9. The method of claim 8, wherein:
the first one of the plurality of probing potential modulation current signals corresponds to a first one of the plurality of voltage steps and the second one of the plurality of probing potential modulation current signals corresponds to a second one of the plurality of voltage steps; or
the first one of the plurality of probing potential modulation current signals and the second one of the plurality of probing potential modulation current signals respectively correspond to the first one of the plurality of voltage steps.

10. The method of claim 1, wherein the continuous analyte monitoring device comprises a wearable sensor portion and a portable user device portion, the sensor defining a part of the wearable sensor portion, and the user interface defining a part of the portable user device portion, and
wherein transmitting the analyte value to the user interface of the continuous analyte monitoring device comprises wirelessly transmitting the analyte value from the wearable sensor portion to the portable user device portion.

11. The method of claim 1, wherein the continuous analyte monitoring device comprises a wearable sensor portion and a portable user device portion, and wherein the method comprises:
determining the analyte value via the wearable sensor portion, and
transmitting the analyte value from the wearable sensor portion to the portable user device portion.

12. The method of claim 1, wherein the continuous analyte monitoring device comprises a wearable sensor portion and a portable user device portion, wherein the method comprises:
transmitting the primary current signal and the plurality of probing potential modulation current signals from the wearable sensor portion to the portable user device portion; and
determining the analyte value via the portable user device portion.

13. The method of claim 1, wherein the sensor comprises a working electrode having a chemical composition selected to oxidize an analyte.

14. The method of claim 13, wherein the analyte is within human interstitial fluid.

15. The method of claim 14, wherein the analyte comprises glucose.

16. The method of claim 13, wherein the analyte comprises at least one of: cholesterol, lactate, uric acid, or alcohol.

17. The method of claim 1, wherein applying the probing potential modulation sequence to the sensor, and determining the plurality of probing potential modulation current signals comprises:
applying an initial probing potential modulation sequence to the sensor during an initial probing period, and determining an initial plurality of probing potential modulation current signals resulting from the initial probing potential modulation sequence; and
periodically applying an intermediate probing potential modulation sequence to the sensor during respective ones of a plurality of intermediate probing periods, and for respective ones of the plurality of intermediate probing periods, determining an intermediate plurality of probing potential modulation current signals resulting from the intermediate probing potential modulation sequence.

18. The method of claim 1, comprising:
determining a plurality of current decay constants and determining the analyte value based at least in part on the plurality of current decay constants,
wherein respective ones of the plurality of current decay constants comprise a ratio of a first one of the plurality of probing potential modulation current signals to a second one of the plurality of probing potential modulation current signals.

19. The method of claim 18, comprising:
modifying a calibration of the continuous analyte monitoring device based at least in part on the plurality of current decay constants.

20. The method of claim 19, wherein the plurality of current decay constants comprise:
a first current decay constant determined during an initial probing period occurring within 30 minutes of inserting the sensor subcutaneously into a subject; and
a second current decay constant determined during an intermediate probing period occurring after a rest period, the rest period temporally separating the initial probing period from the intermediate probing period.

21. The method of claim 19, wherein modifying the calibration of the continuous analyte monitoring device comprises compensating for at least one of the following based at least in part on the plurality of current decay constants:
a difference in sensitivity relative to a center sensitivity, a change in sensitivity over time, a variation attributable to an interference species, and a warmup period of the sensor.

22. The method of claim 1, further comprising:
determining a temperature of the sensor during each of the plurality of voltage steps,
wherein the prediction equation is further determined based on the temperature of the sensor during each of the plurality of voltage steps.

23. A continuous analyte monitoring device, comprising:
a sensor;
a memory;
at least one processor; and
a user interface,
wherein the memory comprises non-transitory computer-executable instructions, which when executed by the at least one processor, causes the continuous analyte monitoring device to perform operations, the operations comprising:
applying a constant voltage potential to the sensor;
determining a primary current signal resulting from the constant voltage potential;
applying a probing potential modulation sequence to the sensor, the probing potential modulation sequence comprising a plurality of voltage steps, the plurality of voltage steps each comprising a change in voltage from the constant voltage potential;
determining a plurality of probing potential modulation current signals resulting from the probing potential modulation sequence;
determining a prediction equation based at least on probing potential modulation current signals determined during at least two voltage steps of the plurality of voltage steps;
determining an analyte value based at least in part on the primary current signal, the plurality of probing potential modulation current signals, and the prediction equation; and
transmitting the analyte value to the user interface.

24. The continuous analyte monitoring device of claim 23, comprising:
a wearable sensor portion comprising the sensor and a wireless transmitter; and
a portable user device portion comprising the user interface and a wireless receiver,
wherein transmitting the analyte value to the user interface comprises wirelessly transmitting the analyte value from the wireless transmitter to the wireless receiver.

25. The continuous analyte monitoring device of claim 23, comprising:
a wearable sensor portion comprising the sensor and a wireless transmitter; and
a portable user device portion comprising the user interface and a wireless receiver,
wherein transmitting the analyte value to the user interface comprises wirelessly transmitting the primary current signal and the plurality of probing potential modulation current signals from the wearable sensor portion to the portable user device portion,
wherein the analyte value is determined via the portable user device portion.

26. The continuous analyte monitoring device of claim 23, wherein applying the probing potential modulation sequence to the sensor, and determining the plurality of probing potential modulation current signals comprises:
applying an initial probing potential modulation sequence to the sensor during an initial probing period, and determining an initial plurality of probing potential modulation current signals resulting from the initial probing potential modulation sequence; and
periodically applying an intermediate probing potential modulation sequence to the sensor during respective ones of a plurality of intermediate probing periods, and for respective ones of the plurality of intermediate probing periods, determining an intermediate plurality of probing potential modulation current signals resulting from the intermediate probing potential modulation sequence.

27. The continuous analyte monitoring device of claim 23, wherein the operations comprise:
determining a plurality of current decay constants and determining the analyte value based at least in part on the plurality of current decay constants,
wherein respective ones of the plurality of current decay constants comprise a ratio of a first one of the plurality of probing potential modulation current signals to a second one of the plurality of probing potential modulation current signals.

28. The continuous analyte monitoring device of claim 27, wherein the operations comprise:
modifying a calibration of the continuous analyte monitoring device based at least in part on the plurality of current decay constants.

29. The continuous analyte monitoring device of claim 28, wherein the plurality of current decay constants comprise:
a first current decay constant determined during an initial probing period occurring within 30 minutes of inserting the sensor subcutaneously into a subject; and
a second current decay constant determined during an intermediate probing period occurring after a rest period, the rest period temporally separating the initial probing period from the intermediate probing period.

30. The continuous analyte monitoring device of claim 28, wherein modifying the calibration of the continuous analyte monitoring device comprises compensating for at least one of the following based at least in part on the plurality of current decay constants:

a difference in sensitivity relative to a center sensitivity, a change in sensitivity over time, a variation attributable to an interference species, and a warmup period of the sensor.

31. The continuous analyte monitoring device of claim 23, wherein the sensor comprises a working electrode having a chemical composition selected to oxidize an analyte.

32. The continuous analyte monitoring device of claim 31, wherein the analyte comprises at least one of: glucose, cholesterol, lactate, uric acid, or alcohol.

33. The continuous analyte monitoring device of claim 31, wherein the analyte is within human interstitial fluid.

34. The continuous analyte monitoring device of claim 23, wherein the continuous analyte monitoring device has a warmup time of less than 30 minutes.

35. The continuous analyte monitoring device of claim 23, wherein the at least two voltage steps used to determine the prediction equation differ from one another in respect of magnitude.

36. The continuous analyte monitoring device of claim 23, wherein the at least two voltage steps used to determine the prediction equation differ from one another in respect of duration.

37. The continuous analyte monitoring device of claim 23, wherein multiple probing potential modulation current signals are determined during each of the at least two voltage steps used to determine the prediction equation.

* * * * *